United States Patent
Nissen et al.

(10) Patent No.: US 9,351,516 B2
(45) Date of Patent: May 31, 2016

(54) **TWO-PHASE FERMENTATION OF *STAPHYLOCOCCUS* INCREASES NITRATE REDUCTASE ACTIVITY**

(71) Applicant: Chr. Hansen A/S, Hoersholm (DK)

(72) Inventors: Carina Nissen, Neustadt am Ruebenberge (DE); Tim Martin Seibert, Marburg (DE)

(73) Assignee: Chr. Hansen A/S, Hoersholm (DK)

( * ) Notice: Subject to any disclaimer, the term of this patent is extended or adjusted under 35 U.S.C. 154(b) by 0 days.

(21) Appl. No.: 14/407,596

(22) PCT Filed: Jun. 14, 2013

(86) PCT No.: PCT/EP2013/062346
§ 371 (c)(1),
(2) Date: Dec. 12, 2014

(87) PCT Pub. No.: WO2013/186348
PCT Pub. Date: Dec. 19, 2013

(65) Prior Publication Data
US 2015/0140171 A1 May 21, 2015

(30) Foreign Application Priority Data
Jun. 15, 2012 (EP) ..................... 12172255

(51) Int. Cl.
| | |
|---|---|
| A23L 1/314 | (2006.01) |
| C12N 1/20 | (2006.01) |
| A23L 1/272 | (2006.01) |
| C12R 1/44 | (2006.01) |
| A23B 4/22 | (2006.01) |
| C12N 9/06 | (2006.01) |
| A23L 1/317 | (2006.01) |
| A23L 1/318 | (2006.01) |
| A23L 1/03 | (2006.01) |

(52) U.S. Cl.
CPC ............. *A23L 1/31481* (2013.01); *A23B 4/22* (2013.01); *A23L 1/0345* (2013.01); *A23L 1/272* (2013.01); *A23L 1/3175* (2013.01); *A23L 1/3182* (2013.01); *A23L 1/3185* (2013.01); *A23L 1/31472* (2013.01); *C12N 1/20* (2013.01); *C12N 9/0044* (2013.01); *C12R 1/44* (2013.01); *A23V 2002/00* (2013.01)

(58) Field of Classification Search
CPC . A23L 1/31481; A23L 1/0345; A23L 1/3185; A23L 1/3182; A23L 1/3175; A23L 1/31472; A23L 1/272; C12N 9/44; C12N 1/20; A23B 4/22; C12R 1/44; A23V 2002/00
USPC ......................................................... 426/56
See application file for complete search history.

(56) References Cited

U.S. PATENT DOCUMENTS

| | | | | |
|---|---|---|---|---|
| 6,689,403 | B1 * | 2/2004 | Gehring ............... | A23B 4/0235 426/266 |
| 2008/0305213 | A1 * | 12/2008 | Husgen .................... | A23B 4/20 426/72 |
| 2011/0300591 | A1 * | 12/2011 | Gilet et al. .................. | 435/128 |
| 2012/0015074 | A1 * | 1/2012 | Draganski ............... | A23B 4/03 426/59 |

FOREIGN PATENT DOCUMENTS

| | | | | |
|---|---|---|---|---|
| FR | WO 2010067148 A1 * | 6/2010 | .............. | A23B 4/22 |
| WO | WO 9961470 A1 * | 12/1999 | ........... | C12N 9/0044 |
| WO | WO-2010/067148 A1 | 6/2010 | | |

OTHER PUBLICATIONS

Pantel et al. "Identification and characterization of the *Staphylococcus carnosus* nitrate reductase operon" Mol Gen Genet (1998) 259: 105-114.*
Neubauer et al. "Physiology and Interaction of Nitrate and Nitrite Reduction in *Staphylococcus carnosus*" Journal of Bacteriology, Apr. 1996, p. 2005-2009.*
Chr. Hansen, Improved taste and color with new meat culture from Chr. Hansen, Aug. 19, 2009, retrieved from the internet, XP-002684970.
Corbiere et al. "Staphylococcal community of a small unit manufacturing traditional dry fermented sausages," International Journal of Food Microbiology, vol. 108, Apr. 2006, pp. 210-217.
Drosinos et al. "Phenotypic and technological diversity of lactic acid bacteria and staphylococci isolated from traditionally fermented sausages in Southern Greece," Food Microbiology, vol. 24, Dec. 2006, pp. 260-270.
Fedtke et al., "The nitrate reductase and nitrite reductase operons and the *narT* gene of *Staphylococcus carnosus* are positively controlled by the novel two-component system NreBC," Journal of Bacteriology, vol. 184, Dec. 2002, pp. 6624-6634.
Gotterup et al., "Colour formation in fermented sausages by meat-associated staphylococci with different nitrite- and nitrate-reductase activities, Meat Science," vol. 78, Jan. 2008, pp. 492-501.
Gotterup et al., "Relationship between nitrate/nitrite reductase activities in meat associated staphylococci and nitrosylmyglobin formation in a cured meat model system," International Journal of Food Microbiology, vol. 120, Nov. 2007, pp. 303-310.
International Search Report dated Oct. 24, 2013 issued in connection with International Application No. PCT/EP2013/062346.
Leroy et al., "Biodiversity of indigenous staphylococci of naturally fermented dry sausages and manufacturing environments of small scale processing units," Food Microbiology, vol. 27, Apr. 2010, pp. 294-301.

(Continued)

*Primary Examiner* — Louise W Humphrey
*Assistant Examiner* — Stephen A Perkins
(74) *Attorney, Agent, or Firm* — Foley & Lardner LLP

(57) ABSTRACT

The present invention is related to the field of reddening of food products. In particular the present invention relates to a two-phase fermentation method for boosting the nitrate reductase activity of *Staphylococcus* strains with nitrate reductase activity comprising a first aerobic phase in the absence of nitrate and a second anaerobic or oxygen limited phase with continuous nitrate feeding and use of the *Staphylococcus* strains for reddening of meat products.

7 Claims, 13 Drawing Sheets

(56) References Cited

OTHER PUBLICATIONS

Moreno-Vivian et al, "Prokaryotic nitrate reduction: molecular properties and functional distinction among bacterial nitrate reductases," Journal of Bacteriology, vol. 181, Nov. 1999, pp. 6573-6584.

Neubauer et al. "Physiology and interaction of nitrate and nitrite reduction in *Staphyloccocus camosus*," Journal of Bacteriology, vol. 178, Apr. 1996, pp. 2005-2009.

Philippot et al. "Dissimilatory nitrate reductases in bacteria," Biochimica et Biophysica Acta, vol. 1446, May 1999, pp. 1-23.

Schlag et al, "Characterization of the oxygen-responsive NreABC regulon of *Staphylococcus aureus*," Journal of Bacteriology, vol. 190, Dec. 2008, pp. 7847-7858.

Talon et al. "Effect of nitrate and incubation conditions on the production of catalase and nitrate reductase by staphylococci," International Journal of Food Microbiology, vol. 52, Nov. 1999, pp. 47-56.

Shi et al., "Effect of *Staphylococcus camosus* Powder on the Color of Sausage," Meat Research, vol. 26, No. 2, pp. 4-7, Feb. 28, 2012.

* cited by examiner

TWO-PHASE FERMENTATION OF STAPHYLOCOCCUS INCREASES NITRATE REDUCTASE ACTIVITY

CROSS REFERENCE TO RELATED APPLICATIONS

The present application is the U.S. National Stage of International Application No. PCT/EP2013/062346, filed Jun. 14, 2013, which claims priority to European Patent Application No. 12172255.7, filed Jun. 15, 2012.

FIELD OF THE INVENTION

The present invention is related to the field of reddening of food products. In particular the present invention relates to a two-phase fermentation method for boosting the nitrate reductase activity of *Staphylococcus* strains with nitrate reductase activity comprising a first aerobic phase in the absence of nitrate and a second anaerobic or oxygen limited phase with continuous nitrate feeding and use of the *Staphylococcus* strains for reddening of meat products.

BACKGROUND ART

Color formation and color stability are amongst the most critical quality traits of processed meat products and thus of great importance to the meat industry. The characteristic cured color can be derived from the concentration of heme pigments (myoglobin, hemoglobin), their chemical states and additives such as nitrogen oxides and reducing agents. In standard fermented meat products, such as salami, the characteristic cured color is a result of the chemical reaction between compounds derived from added nitrite/nitrate and the naturally occurring red myoglobin leading to the simultaneous formation of the bright red nitrosylmyoglobin, in which an axial ligand nitric oxide (NO) is coordinated to the central $Fe^{2+}$ in heme.

Despite of all its desired properties (color formation, microbiologic safety), the safety of nitrite to human health has been questioned. Nitrite can cause the formation of unwanted compounds in cured meat, like N-nitrosamines which are questionable in regard to health. These compounds can be formed in principle due to the reaction of nitrite with secondary amines and amino acids in muscle proteins as well as in the gastrointestinal tract.

The use of *Staphylococcus* strains for color formation is based on their ability to reduce inorganic nitrate to nitrite which is further degraded into the above described nitric oxide (NO), the active compound in the color formation process. The nitrate could be provided directly as nitrate salt or indirectly with a natural nitrate source (vegetable powders). Even if a nitrite salt is added, the addition of *Staphylococcus* strains is recommended as nitrite is partially re-converted to nitrate.

*Staphylococcus carnosus* and less frequently *Staphylococcus xylosus* are standard *Staphylococcus* strains used for the purpose of nitrate reduction and color formation. These strains are properly working at higher fermentation temperatures but are less active at low temperatures, below 6° C. As low production temperatures are preferred by the industry due to hygiene reasons a *Staphylococcus* strain having nitrate reductase activity at low temperatures is wanted.

*Staphylococcus vitulinus* is a strain known to have nitrate reductase activity at low temperatures and it has been used in combination with lactic acid bacteria for reddening of meat (WO2010/067148).

However, there is a need for methods which improve the nitrate reduction and color formation in food products and as a result may lead to a decrease in the production time necessary for the desired reddening of the food products and thereby lead to reduction in cost of production of such products.

SUMMARY OF THE INVENTION

The inventors of the present invention have surprisingly found that when producing a *Staphylococcus* strain having nitrate reductase activity by a two-phase fermentation involving a first phase of fermenting the strain under high aeration in the absence of nitrate and a second phase of fermenting the strain under low aeration while continuously feeding nitrate the *Staphylococcus* strain develops an increased nitrate reductase activity leading to an increased reddening when used for coloring of food products containing myoglobin.

Therefore, in a first aspect the present invention relates to a method for increasing the nitrate reductase activity of a *Staphylococcus* strain having nitrate reductase activity comprising the steps of
 a) fermenting the strain in the absence of nitrate under aerobic conditions;
 b) fermenting the strain under anaerobic or oxygen limiting conditions while continuously feeding nitrate to the fermentation medium; and
 c) optionally pelletizing and optionally freeze-drying the strain.

In a second aspect the present invention is directed to a *Staphylococcus* strain obtainable by the method according to the first aspect, wherein the nitrate reductase activity of the strain cannot be improved by more than 50%.

In a third aspect the present invention relates to a *Staphylococcus vitulinus* strain selected from the group consisting of the *Staphylococcus vitulinus* strain CHCC10896 was deposited with the Deutsche Sammlung von Mikroorganismen und Zellkulturen (DSMZ) under the accession no. DSM 25789 and mutants derived thereof.

The fourth aspect of the present invention relates to a method for reddening of a food product comprising the steps of
 a) pre-treating a *Staphylococcus* strain having nitrate reductase activity according to the method of the first aspect of the invention;
 b) adding the pre-treated *Staphylococcus* strain to a food product; and
 c) fermenting, ripening or curing the food product with the pre-treated *Staphylococcus* strain.

A fifth aspect of the present invention is directed to a food product comprising a *Staphylococcus* strain according to the second or third aspect of the invention.

In a sixth aspect the present invention relates to use of a *Staphylococcus* strain according to the second or third aspect for reddening of a food product.

A seventh aspect relates to a food product obtainable by the method according to the first aspect of the present invention or a food product obtainable by the use according to the sixth aspect of the invention.

DETAILED DESCRIPTION OF THE INVENTION

Figure 1:
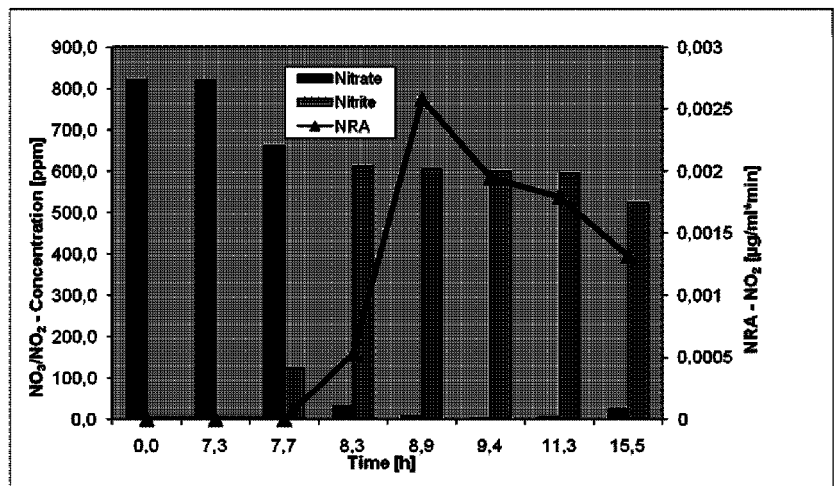
FIG. 1 depicts the development of nitrate/nitrite concentration as well as the nitrate reductase activity (NRA) during standard fermentation with *Staphylococcus vitulinus* strain CHCC10896.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The present invention relates to a method of fermenting a *Staphylococcus* strain having nitrate reductase activity under certain conditions in order to increase the nitrate reductase activity of the *Staphylococcus* strain.

The term "*Staphylococcus* strain having nitrate reductase activity" as used herein refers to a *Staphylococcus* strain which is capable of converting nitrate to nitrite.

The fermentation is carried out as a two-phase fermentation wherein the first phase comprises fermenting the strain in the absence of nitrate under aerobic conditions and wherein the second phase comprises fermenting the strain under anaerobic or oxygen limiting conditions while continuously feeding nitrate to the fermentation medium. Finally, the strain may optionally be pelletized and/or freeze-dried.

The term "in the absence of nitrate" as used herein refers to fermentation carried out in fermentation medium wherein no nitrate has been added.

The term "fermentation medium" is intended to mean a fermentation medium which allows the production of bacterial metabolites and/or the growth of biomass.

In a preferred embodiment the aerobic conditions of the first phase comprises fermenting the strain under high aeration of at least 0.5 vvm (volume per volume per minute), such as at least 0.6 vvm, such as at least 0.7 vvm, such as at least 0.8 vvm.

In a preferred embodiment the first phase is continued for 5 to 12 hours, such as from 6 to 10 hours.

In another preferred embodiment the first phase is continued until the partial pressure of oxygen ($pO_2$) of the fermentation medium reaches 0.

The $pO_2$ of the fermentation medium may be measured with optical dissolved oxygen sensors as described in Example 2 herein.

The term "continuously feeding nitrate" as used herein refers to either a steady addition of nitrate to the fermentation medium or an addition of nitrate to the fermentation medium in pulses of no longer than 15 min. between each addition of a constant amount of nitrate.

In a preferred embodiment the nitrate is added in pulses of no longer than 10 min. such as in pulses of no longer than 8 min., such as in pulses of no longer than 6 min., such as in pulses of no longer than 5 min.

The nitrates useful for the method according to the present invention may be of chemical origin. They may, for example, be potassium nitrate, sodium nitrate, saltpeter, and mixtures thereof.

The nitrates may also be of natural origin. They may, for example, be provided by plants and/or extracts of plants which are advantageously chosen from plants naturally rich in nitrates, such as e.g. leek, celery, onion, spinach and cabbage.

The nitrates may be provided in liquid and solid form.

In a preferred embodiment the feeding of nitrate in the second phase is at a rate of from 0.5 to 2.0 g/(l*h), such as from 0.8 to 1.8 g/(l*h).

The term "oxygen limiting conditions" as used herein is intended to encompass any conditions restricting accessible oxygen, typically by controlled aeration, including such low aeration that the strain is effectively experiencing near-anaerobic growth.

In a preferred embodiment the second anaerobic or oxygen limited phase comprises fermenting the strain under aeration of at the most 0.08 vvm, such as at the most 0.07 vvm, such as at the most 0.06 vvm, such as at the most 0.05 vvm, such as at the most 0.04 vvm, such as at the most 0.03 vvm.

Without wishing to be bound by theory, it is believed that the lack of oxygen in the second phase stresses the strain to increase expression from the nar operon responsible for nitrate reductase activity which is facilitated by a high continuous concentration of nitrate. During aerobic respiration electrons provided by an electron donor like NADH are transferred by the electron transport chain to the terminal reductase to be transferred to the final electron acceptor O2. During this process a protein motive force is formed by separating electrons and protons by the membrane. By an influx of protons into the cell via the membrane bound ATP-synthase ATP is formed. Under anaerobic condition, during the lack of oxygen, an alternative electron acceptor is needed to keep this process running, e.g. nitrate. The nitrate is thereby reduced into nitrite by the nitrate reductase.

The *Staphylococcus* strain may be any *Staphylococcus* strain having nitrate reductase activity such as e.g. a *Staphylococcus vitulinus*, a *Staphylococcus carnosus* or a *Staphylococcus xylosus* strain.

In a preferred embodiment of the present invention the *Staphylococcus* strain having nitrate reductase activity is a *Staphylococcus vitulinus* strain or a *Staphylococcus carnosus* strain having nitrate reductase activity.

In a more preferred embodiment the *Staphylococcus* strain having nitrate reductase activity is a *Staphylococcus vitulinus* strain.

In a much preferred embodiment of the present invention the *Staphylococcus vitulinus* strain is selected from the group consisting of the *Staphylococcus vitulinus* strain CHCC10896 that was deposited with the Deutsche Sammlung von Mikroorganismen und Zellkulturen (DSMZ) under the accession no. DSM 25789, the *Staphylococcus vitulinus* strain CHCC11576 that was deposited with the Deutsche Sammlung von Mikroorganismen und Zellkulturen (DSMZ) under the accession no. DSM 27311 and mutants derived thereof.

In the present context, the term "mutant" should be understood as a strain derived from a strain of the invention by means of e.g. genetic engineering, radiation and/or chemical treatment. It is preferred that the mutant is a functionally equivalent mutant, e.g. a mutant that has substantially the same, or improved, properties (e.g. regarding nitrate reductase activity) as the mother strain. Such a mutant is a part of the present invention. Especially, the term "mutant" refers to a strain obtained by subjecting a strain of the invention to any conventionally used mutagenization treatment including treatment with a chemical mutagen such as ethane methane sulphonate (EMS) or N-methyl-N'-nitro-N-nitroguanidine (NTG), UV light or to a spontaneously occurring mutant. A mutant may have been subjected to several mutagenization treatments (a single treatment should be understood one mutagenization step followed by a screening/selection step), but it is presently preferred that no more than 20, or no more than 10, or no more than 5, treatments (or screening/selection steps) are carried out. In a presently preferred mutant less than 1%, less than 0.1, less than 0.01, less than 0.001% or even less than 0.0001% of the nucleotides in the bacterial genome have been replaced with another nucleotide, or deleted, compared to the mother strain.

The present invention also relates to a *Staphylococcus* strain obtainable by the method described above. The nitrate reductase activity of the *Staphylococcus* strain which has been subjected to the two-phase fermentation method described above cannot be improved to the same extent as the nitrate reductase activity of the *Staphylococcus* strain which has not been subjected to the two-phase fermentation of the invention.

Thus, subjecting the *Staphylococcus* strain, which has been subjected once to the two-phase fermentation method, to e.g. a second round of the two-phase fermentation method within the following hours will not improve the nitrate reductase activity of the strain to the same extent as when the strain is first subjected to the two-phase fermentation method. The exact period between the time points where the strain is subjected to the first and second round of the two-phase fermentation method and still maintains a high nitrate reductase activity depends on various conditions like the presence of oxygen and the temperature at which the samples are kept.

Preferably, the percentage by which the nitrate reductase activity can be improved is determined by subjecting the strain to the two-phase fermentation method no more than 3 hours after producing the strain and keeping the strain at a temperature below 5° C. and under anaerobic conditions.

Without wishing to be bound by theory, it is believed that other methods—than the two-phase fermentation method of the invention—for increasing nitrate reductase activity to levels above those achieved by standard fermentation in a *Staphylococcus* strain may exist. It may e.g. be possible to induce the nar operon responsible for nitrate reductase activity by subjecting the strains to other stress factors.

In a preferred embodiment the nitrate reductase activity of the strain cannot be improved by more than 50%, such as by more than 40%, such as by more than 30%, such as by more than 20%, such as by more than 10%.

The percentage improvement of the nitrate reductase activity of a *Staphylococcus* strain in question can be readily determined by using the method for determination of nitrate reductase activity as described in the Examples herein: The nitrate reductase activity is determined for the strain in question before and after subjecting the strain to the two-phase fermentation method according to the invention and the improvement in the nitrate reductase activity can be calculated by determining the increase in nitrate reductase activity.

In a preferred embodiment the *Staphylococcus* strain is obtained by the method described above.

In another preferred embodiment the *Staphylococcus* strain when added in an amount of $3.6 \times 10^{10}$ CFU/kg of meat and used for preparation of a mortadella-type sausage fermented at 12° C. for 21 hours is capable of reddening the meat to a red color intensity (a*-value) according to the L*a*b*-color system of at least 14. The mortadella-type sausage may be prepared according to Examples 3 and 4 herein.

In yet another preferred embodiment of the present invention the *Staphylococcus* strain when added in an amount of $1.5 \times 10^{10}$ CFU/kg of meat and used for preparation of cooked ham fermented at 6° C. for 16 hours is capable of reddening the meat to a red color intensity (a*-value) according to the L*a*b* system of at least 10, such as at least 11, such as at least 12.

The cooked ham may be prepared according to Example 5 herein.

The present invention also relates to a *Staphylococcus vitulinus* strain selected from the group consisting of the *Staphylococcus vitulinus* strain CHCC10896 that was deposited with the Deutsche Sammlung von Mikroorganismen und Zellkulturen (DSMZ) under the accession no. DSM 25789 and mutants derived thereof.

In the present context, the term "mutant" should be understood as a strain derived from a strain of the invention by means of e.g. genetic engineering, radiation and/or chemical treatment. It is preferred that the mutant is a functionally equivalent mutant, e.g. a mutant that has substantially the same, or improved, properties (e.g. regarding nitrate reductase activity) as the mother strain. Such a mutant is a part of the present invention. Especially, the term "mutant" refers to a strain obtained by subjecting a strain of the invention to any conventionally used mutagenization treatment including treatment with a chemical mutagen such as ethane methane sulphonate (EMS) or N-methyl-N'-nitro-N-nitroguanidine (NTG), UV light or to a spontaneously occurring mutant. A mutant may have been subjected to several mutagenization treatments (a single treatment should be understood one mutagenization step followed by a screening/selection step), but it is presently preferred that no more than 20, or no more than 10, or no more than 5, treatments (or screening/selection steps) are carried out. In a presently preferred mutant less than 1%, less than 0.1, less than 0.01, less than 0.001% or even less than 0.0001% of the nucleotides in the bacterial genome have been replaced with another nucleotide, or deleted, compared to the mother strain.

The present invention furthermore relates to a method for reddening of a food product comprising the steps of pre-treating a *Staphylococcus* strain having nitrate reductase activity according to the method of fermenting a *Staphylococcus* strain having nitrate reductase activity described above, adding the pre-treated *Staphylococcus* to a food product, and fermenting, ripening or curing the food product with the pre-treated *Staphylococcus* strain.

The food product may be any product based on a food source containing myoglobin. In a preferred embodiment the food product is a meat product.

The meat product may be any product with a content of meat. The meat may be bovine meat, pork meat, poultry meat, game meat or any other category of meat.

The food product may also be a product based on fish and/or based on crustaceans.

In a preferred embodiment the *Staphylococcus* strain is added in a quantity of from $1.0\times10^8$ to $1.0\times10^{12}$ CFU/kg, such as from $1.0\times10^9$ to $1.0\times10^{11}$ CFU/kg. Preferably the *Staphylococcus* strain is added in a quantity of from $2.0\times10^9$ to $5.0\times10^{10}$ CFU/kg.

In a preferred embodiment the fermenting, ripening or curing of the food product with the pre-treated *Staphylococcus* strain takes place at a temperature of from 4° C. to 45° C., such as at a temperature of from 4° C. to 30° C., such as at a temperature of from 4° C. to 25° C.

The fermenting, ripening or curing of the food product may last for from 8 hours to several days/weeks.

In a preferred embodiment the *Staphylococcus* strain is a *Staphylococcus vitulinus* strain or a *Staphylococcus carnosus* strain.

In a more preferred embodiment the *Staphylococcus* strain is a *Staphylococcus vitulinus* strain.

In a much preferred embodiment the *Staphylococcus vitulinus* strain is selected from the group consisting of the *Staphylococcus vitulinus* strain CHCC10896 that was deposited at the Deutsche Sammlung von Mikroorganismen und Zellkulturen (DSMZ) under accession no. DSM 25789, the *Staphylococcus vitulinus* strain CHCC11576 that was deposited with the Deutsche Sammlung von Mikroorganismen und Zellkulturen (DSMZ) under the accession no. DSM 27311 and mutants derived thereof.

In the present context, the term "mutant" should be understood as a strain derived from a strain of the invention by means of e.g. genetic engineering, radiation and/or chemical treatment. It is preferred that the mutant is a functionally equivalent mutant, e.g. a mutant that has substantially the same, or improved, properties (e.g. regarding nitrate reductase activity) as the mother strain. Such a mutant is a part of the present invention. Especially, the term "mutant" refers to a strain obtained by subjecting a strain of the invention to any conventionally used mutagenization treatment including treatment with a chemical mutagen such as ethane methane sulphonate (EMS) or N-methyl-N'-nitro-N-nitroguanidine (NTG), UV light or to a spontaneously occurring mutant. A mutant may have been subjected to several mutagenization treatments (a single treatment should be understood one mutagenization step followed by a screening/selection step), but it is presently preferred that no more than 20, or no more than 10, or no more than 5, treatments (or screening/selection steps) are carried out. In a presently preferred mutant less than 1%, less than 0.1, less than 0.01, less than 0.001% or even less than 0.0001% of the nucleotides in the bacterial genome have been replaced with another nucleotide, or deleted, compared to the mother strain.

Furthermore, the present invention relates to a food product comprising a *Staphylococcus* strain obtainable by the two-phase method of fermentation as described above or a *Staphylococcus* strain selected from the group consisting of the *Staphylococcus vitulinus* strain CHCC10896 that was deposited at DSMZ under the accession no. DSM 25789, the *Staphylococcus vitulinus* strain CHCC11576 that was deposited with the Deutsche Sammlung von Mikroorganismen und Zellkulturen (DSMZ) under the accession no. DSM 27311 and mutants derived thereof, which have been subjected to the two-phase method of fermentation as described above. In a preferred embodiment of the present invention the *Staphylococcus* strain is obtained by the two-phase method of fermentation as described above.

In a preferred embodiment the food product is a meat product.

In a preferred embodiment, the meat product is a mortadella-type sausage, wherein the mortadella-type sausage has a red color intensity (a*-value) according to the L*a*b*-system of at least 14.

In another preferred embodiment, the meat product is a cooked ham, wherein the cooked ham has a red color intensity (a*-value) according to the L*a*b*-system of at least 10, such as at least 11, such as at least 12.

The present invention in addition relates to the use of a *Staphylococcus* strain obtainable by the two-phase method of fermentation as described above or a *Staphylococcus* strain, which has been subjected to the two-phase method of fermentation as described above and selected from the group consisting of the *Staphylococcus vitulinus* strain CHCC10896 that was deposited at DSMZ under the accession no. DSM 25789, the *Staphylococcus vitulinus* strain CHCC11576 that was deposited with the Deutsche Sammlung von Mikroorganismen und Zellkulturen (DSMZ) under the accession no. DSM 27311 and mutants derived thereof for reddening of a food product.

In a preferred embodiment the *Staphylococcus* strain is obtained by the two-phase method of fermentation as described above.

Preferably, the food product is a meat product.

The invention also is directed to a food product obtainable by the method for reddening a food product described above or a food product obtainable by the use described above.

Embodiments of the present invention are described below, by way of non-limiting examples.

EXAMPLES

Method for Determination of Nitrate Reductase Activity

The following method can be used for determining nitrate reductase activity (NRA):

In a first step, approximately $5\times10^8$ cfu/ml are incubated statically in an induction buffer (10 g/l tryptone, 1 g cystein, 1 g KNO3; pH 7.0) at 30° C. in Eppendorf reaction cups. The temperature and incubation time is adapted to the particular problem which should be evaluated. It is important to reduce the oxygen supply of the cells within the induction buffer to a minimum by minimizing the air phase above the suspension, e.g. by using a mineral oil for covering. By using the same cell count, incubation time and temperature every time, the results are comparable from one assay to another but it is also suitable to dose the cells by $OD_{600}$ measurement if a fast analysis is needed and no cell count is available. For example when isolates stored on agar plates should be tested for nitrate reductase activity the inoculation of the induction buffer should be carried out according to $OD_{600}$ measurement. Here it is important to incubate a colony from agar dishes over day in a suitable medium and to inoculate a suitable volume of fresh medium in the evening which is then incubated overnight. The samples which should be compared to each other should have a comparable optical density that one could act on the assumption that all samples show more or less the same ratio of live and dead cells, what makes the dosing by $OD_{600}$ measurement feasible. From these overnight cultures one could inoculate the induction buffer to the same $OD_{600}$ of all samples. The $OD_{600}$ should not exceed 0.6 as an optical density higher than 0.6 is tempering the results.

The step of induction is important as it somehow mimics the conditions which would also take place in the final product when applying cultures for color stability in meat. The nitrate reductase system of *Staphylococci* is induced by anaerobic conditions in the presence of nitrate as it is the case within the meat product. The regulatory process of inducing the nitrate reduction system (transcription, protein biosynthesis) takes some time within the meat product, therefore it was thought to use an induction step to give the cells the time to "reactivate" the nitrate reduction system as it would take place in the meat product.

The assay itself is based on a method developed by Lowe and Evans (Lowe and Evans (1964). Biochimica et biophysica acta 85; 377-389) wherein the reaction velocity is determined by measuring the production of nitrite from nitrate in a dithionite/benzyl viologen system.

A reaction mixture is used, consisting of potassium phosphate buffer (100 mM; pH 7.0), benzyl viologen (30 mM) as artificial electron donor, potassium nitrate (12 mM) and the reducing agent dithionite (141 mM). The addition of dithionite in excess facilitates the handling under laboratory conditions without anoxic chamber. The reaction is started by the addition of the bacterial cells.

Reaction Mixture:

| | | |
|---|---|---|
| 0.2 ml | pre-induced cell suspension | |
| 10.8 ml | potassium phosphate buffer | (100 mM; pH 7.0) |
| 0.4 ml | KNO3 solution | (12 mM) |
| 0.4 ml | benzyl viologen solution | (30 mM) |

Preheat the test tube in a water bath at 30° C. for 2 min by slow stirring.

| | | |
|---|---|---|
| 0.4 ml | dithionite solution | (141 mM) |

Incubate the test tube within the water bath and transfer 0.4 ml of this solution to Eppendorf cups at various time intervals (e.g. 0, 5, 10, 20, 30 and 60 minutes)

The samples should be aerated by shaking immediately after sampling until discoloration of the reduced benzyl viologen The cup is then centrifuged at 10.000×g for 3 minutes 50 µl of the supernatant is transferred to a well of a 96-well micro titer plate (at least 5 wells)

250 µl of the Griess-reagent is added to each well

Store the plate in the dark for 10 min

Read absorbency at 540 nm with microplate reader

Absorbency should not exceed 0.8 otherwise dilution is necessary

Remarks

As control it is suitable not to add any cells or nitrate. One could create a standard graph where samples of known nitrite concentration are used and calculate the molar extinction coefficient which corresponds to the slope of the line. With the help of the molar extinction coefficient and the measured absorbency it is possible to calculate the nitrite concentrations at the particular time. By implementing the time factor one could calculate the enzyme activity but it is also suitable only to take the absorbency at 540 nm as a direct indication of nitrate reductase activity.

Method for Determination of Nitrate and Nitrite in Meat and Meat Products.

The following method can be used for determining nitrate and nitrite concentrations:

Principle of Determination

The sample is extracted with hot water and the extract is filtrated after the denaturation of the protein content. The filtrate contains the extracted nitrate and nitrite. Nitrite can be determined directly by the Griess reaction by adding sulphanilamide (color reagent I) and N-(1-Naphthyl-)-ethylendiammoniumdichloride (color reagent II). The product of this reaction, a chromphor with an absorption maximum at 546 nm, shows a pink color and can be determined photometrically. Nitrate cannot be determined directly, it has to be reduced to nitrite first. The reduction is done by flow-through of the filtrate via a reduction column containing metallic cadmium as the reducing agent. The difference between the amount of nitrite determined after the reduction via the cadmium column (total nitrite) minus the amount determined within the filtrate directly after extraction (nitrite) gives the amount of nitrate within the sample.

Experimental

The cadmium slurry is prepared by dissolving 60-70 g cadmiumsulphate (3CdSO4×8 H2O) in 600 ml deionized water. For precipitation of cadmium 3-5 zinc-batons are dipped into the solution. The precipitated cadmium is harvested by decantation after 6-8 h. The precipitate is washed in 2×1000 ml of deionized water. The washed precipitate is mixed with 400 ml 0.1 M HCl and incubated overnight in HCl. The reduction column is prepared by putting glass wool into the taper of the glass column for retention of the cadmium slurry. After decantation of the HCl the cadmium slurry is washed into the column with deionized water until reaching a height of about 170 mm. Inclusions and air bubbles should be avoided and need to be removed if appearing. The column should allow a flow through of 6-9 ml/min.

The meat samples are homogenized by grinding. Approximately 10 g of sample (exact weight is noted for calculation) is weighed into an 100 ml Erlenmeyer flask. 10 ml of a saturated sodium borate solution (50 g/l of disodiumtetraborate-decahydrate dissolved in warmed deionized water) and 50 ml of deionized water are added. The suspension is mixed thoroughly and heated to 95° C. for 15 min. Afterwards, the suspension is quantitatively transferred to a 200 ml volumetric flask and heated again at 95° C. for 15 min. The suspension is mixed periodically. Subsequently, 5 ml of Carrez I (106 g/l potassiumhexacyanoferrate(II)-trihydrate dissolved in deionized water; the solution has to be stored in a brown bottle and has to be prepared weekly) and Carrez II solution (220 g zinc acetate in 30 ml pure acetic acid and filled up to 1000 ml with deionized water) is added to denature residual protein. The suspension is mixed thoroughly. If needed, depending on the nature of the sample (e.g. high fat content) the amount of Carrez solutions can be increased. After cooling to room temperature, the volumetric flask is filled with deionized water to the mark and mixed. The sample solution is filtrated by a filter for medium-fine precipitates. The first part of the filtrate is discarded; the filtrate has to be clear and colorless.

For the determination of nitrite, 10 ml of filtrate is transferred to a 100 ml flask by adding 5 ml of color reagent I (6 g sulfanilamide dissolved in 500 ml deionized water by heating, added 250 ml HCl (37%) by permanent agitation after cooling and filled up to 1000 ml with deionized water) and color reagent II (0.25 g N-(1-Naphthyl)ehylendiammonium-dichloride dissolved in 250 ml deionized water; the solution has to be stored in a brown bottle and has to be prepared weekly). The solution is incubated in the dark for 30 min at room temperature. In the following the extinction of the solution is determined photometrically at 546 nm against a blind (Color reagent I and II+deionized water in a relation of 1:2).

For the determination of nitrate, 20 ml of the filtrate is transferred into a 100 ml flask by adding 5 ml of ammonia-buffer (20 ml HCl (37%) diluted in 500 ml of deionized water, added 10 g Titriplex III (EDTA) and 55 ml ammonia solution (25%) and filled up to 1000 ml with deionized water; pH 9.6-9.7). The mixed solution is transferred to the reduction column. The column has to be prepared before by flow through of 25 ml HCl (0.1M), 50 ml deionized water and 25 ml of diluted ammonia-buffer solution (1:10 in deionized water). The column should never run dry. The eluate for the nitrate determination is collected in a 100 ml volumetric flask. After the whole filtrate is added the column is washed 3-4 times with approximately 15 ml of deionized water. The flow through is also collected in the volumetric flask. The volumetric flask which is now containing the reduced sample solution is filled up to the mark with deionized water and mixed thoroughly.

For the determination of nitrite/reduced nitrate, 10 ml of filtrate are transferred to a 100 ml flask by adding 5 ml of color reagent I and II. The solution is incubated in the dark for 30 min at room temperature. In the following the extinction of the solution is determined photometrically at 546 nm against a blind (Color reagent I and II+deionized water in a relation of 1:2).

Calculations

The nitrite concentration, indicated as $NaNO_2$ in ppm [mg/kg], is calculated as follows:

$$\text{Nitrite concentration[ppm]} = a*V/E_W, \text{ wherein}$$

a: µg $NaNO_2$ (this value can be read directly from a calibration line after determination of the extinction of the sample at 546 nm. The calibration line is generated by determining the extinction at 546 nm of solutions with known nitrite concentration) within the sample directly after extraction.
V: Dilution factor.
$E_W$: Sample weight in g.

The total nitrite concentration, indicated as $NaNO_2$ in ppm [mg/kg], is calculated as follows:

$$\text{Total nitrite concentration[ppm]} = b*V/E_W, \text{ wherein}$$

b: µg $NaNO_2$ (this value can be read directly from a calibration line after determination of the extinction of the sample at 546 nm. The calibration line is generated by determining the extinction at 546 nm of solutions with known nitrite concentration) originally in the sample plus the nitrite which is derived from nitrate by reduction via the cadmium column.
V: Dilution factor.
$E_W$: Sample weight in g.

The nitrate concentration, indicated as $KNO_3$ in ppm [mg/kg], is calculated as follows:

$$\text{Nitrite from nitrate concentration[ppm]} = \text{total nitrite concentration[ppm]} - \text{nitrite concentration[ppm]}$$

$$\text{Nitrate concentration[ppm]} = \text{nitrite from nitrate concentration[ppm]} \times 1,465 \text{(conversion factor from nitrite to nitrate)}$$

Example 1

Standard Fermentation Procedure for *Staphylococcus* Species

Experimental:

The fermentations were carried out in a modified version of the standard glycerol medium which is used for *Staphylococcus carnosus* MIII. The content of glycerol is reduced compared to the standard medium used for *Staphylococcus carnosus* MIII to ensure a sufficient supply with oxygen.

Fermentation Medium:

| Object description | % | weight (g) |
|---|---|---|
| Water | 91.20 | 10944.00 |
| Antifoam-oil Erol DF 204K | 0.20 | 24.00 |
| Potassium nitrate | 0.10 | 12.00 |
| Yeast Extract - HyYest 412 (Sheffield Bioscience) | 5.00 | 600.00 |
| Glycerol 99.5% | 3.50 | 420.00 |
| SUM | 100.00 | 12000.00 |

Fermentation medium was prepared and the pH was adjusted to 7.2 prior to sterilization by autoclaving at 121° C. for 20 min. pH was adjusted to 7.2 and *Staphylococcus vitulinus* strain CHCC10896 was inoculated at 0.1% (approx. $2.6 \times 10^7$.

Fermentation was carried out at 37° C. with 500 rpm agitation and an air flow of 0.5 (6 L/min) for 15.5 hours.

Samples were taken during the whole fermentation process at the time points shown in FIG. 1. The samples were analyzed with regard to nitrate/nitrite concentration.

Results

The results show that the strain (*Staphylococcus vitulinus* CHCC10896) is reducing nitrate to nitrite after approximately 6-8 hours of fermentation. This indicates a drop in oxygen supply at this time point most likely caused by an increase in cell density. The transcription of the nar operon (nitrate reduction) is induced under anoxic conditions in the presence of nitrate and inhibited by the presence of oxygen. FIG. 1 that the NRA is increasing between 8 and 9 hours to certain level, where a drop in oxygen supply most likely occurs. The NRA is highest around 9 hours of fermentation and is then decreasing again most likely due to the lack of nitrate which is promptly reduced when the strain is not supplied with sufficient oxygen anymore. However, the high level of nitrite which is not further reduced to ammonia by *Staphylococcus vitulinus* is also known to induce the nar operon. This could explain that there is only a slight decrease in NRA at end of fermentation. From the shown data it can be clearly seen that the strain is rapidly running out of nitrates and this might explain the reduced NRA of the strain when produced by the standard 1-phase fermentation procedure.

To improve the NRA of *Staphylococcus vitulinus* it was suggested to run a fermentation procedure divided into two phases. Within the first phase the strain has to be supplied with sufficient oxygen to generate biomass efficiently. Within the second phase the process should be switched from aerobic to anaerobic or oxygen limiting conditions accompanied by a continuous feed of nitrate. It has to be avoided that the strain is running out of nitrate during anaerobic or oxygen limited growth until the end of fermentation.

Example 2

Adaptation of Standard Fermentation Procedure to a 2-Step Process

The adapted fermentation procedure for optimizing the NRA of *Staphylococcus vitulinus* strain CHCC10896 can be divided into two phases. The purpose of the first phase is the development of biomass while the strain is aerated sufficiently whereas the second phase is for conditioning to optimize/increase the NRA by reducing aeration and feeding with continuous pulses of nitrate until the end of fermentation. In total two fermentations were carried out by applying the above roughly described process. The fermentations were carried out in a modified version of the standard glycerol medium which is used for *Staphylococcus carnosus* MIII. The content of glycerol is reduced compared to the standard medium used for *Staphylococcus carnosus* MIII to ensure a sufficient supply with oxygen during the first, aerated fermentation phase. In total 4 fermentations were carried out, 2 by leaving out nitrate which is used by default in the standard glycerol medium. However, the nitrate feeding was applied in both cases after decreasing the aeration.

Experimental

A batch of fermentation medium was prepared according to the recipe in Example 1 a batch of fermentation medium without nitrate was prepared. The pH of both media was adjusted to 7.2 prior to sterilization by autoclaving at 121° C. for 20 min. pH was adjusted to 7.2 again and *Staphylococcus vitulinus* strain CHCC10896 was inoculated at 0.1% (approx. $2.6 \times 10^7$ CFU/ml) into each fermentation media.

The dissolved oxygen content ($pO_2$) in the fermentation medium was measured with optical dissolved oxygen sensors (Mettler Toledo InPro6870i/120).

Fermentation was carried out at 37° C. with 500 rpm agitation and an air flow of 0.5 (6 L/min) until $pO_2$ reached 0 (approximately 6.3 hours). Then the air flow was reduced to 0.08 vvm (1 L/min) and nitrate feed (0.17 g/L potassium nitrate with 10 pulses=1.02 g/(l*h)) was started.

The fermentation was carried out for approximately 19 hours in total.

Then the fermentation was cooled down to 15° C. and the cells were harvested.

Samples of the fermentations described above were taken at different time points and analyzed with regard to nitrate and nitrite concentration. The results of the analyses are shown in FIGS. 2 (no nitrate added to the initial fermentation medium) and 3 added to the initial fermentation medium).

Results

The results (FIGS. 2 and 3) clearly show that the strain *Staphylococcus vitulinus* CHCC10896 is sufficiently converting/reducing nitrate into nitrite as soon as it is not supplied with sufficient oxygen anymore. As no nitrate is accumulating during the feeding phase, the NRA seems to be rather high. However, the maximum activity of CHCC10896 might not be reached yet as the nitrite concentration is still increasing while nitrate is completely reduced. If the maximal activity would have been reached, nitrate should have accumulated and the nitrite concentration would not accelerate with the same slope anymore or would even reach a plateau/stationary phase.

Figure 2:
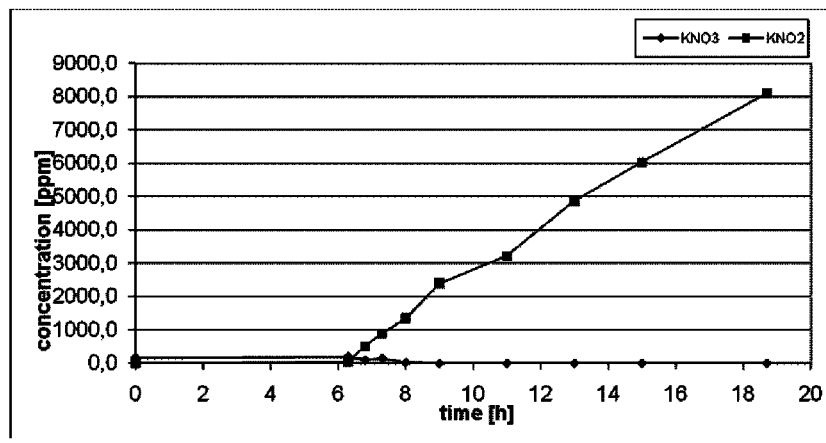
FIG. 2 shows the development of nitrate/nitrite concentration during a two-phase fermentation with *Staphylococcus vitulinus* strain CHCC10896. At time point 6.3 hours the aeration was reduced significantly and the feeding with nitrate was started. No nitrate was added to the batch medium.
Figure 3:
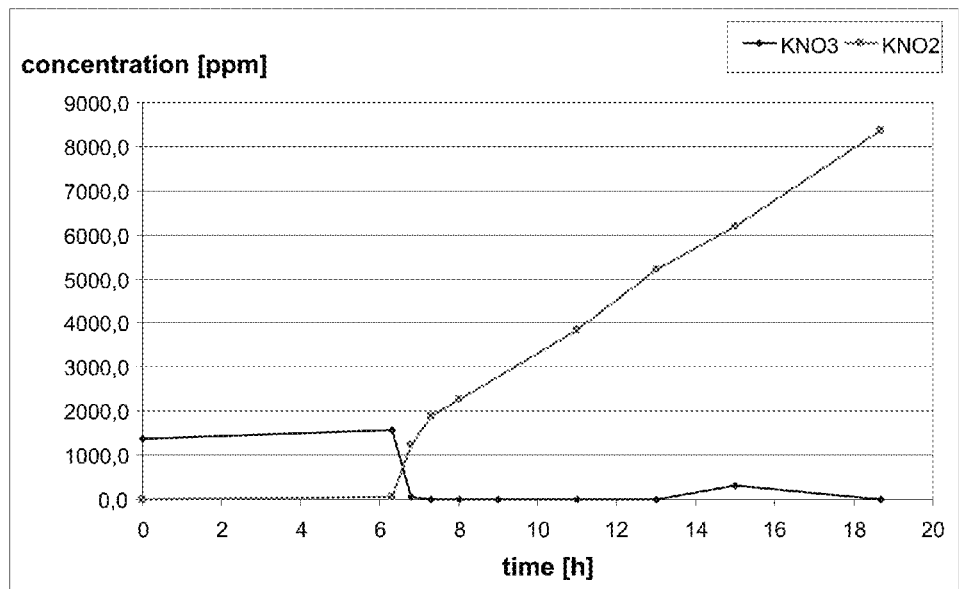
FIG. 3 depicts the development of nitrate/nitrite concentration during a two-phase fermentation with *Staphylococcus vitulinus* strain CHCC10896. At time point 6.3 hours the aeration was reduced significantly and the feeding with nitrate was started. Nitrate was added to the batch medium.

When nitrate is added in the medium from the beginning (FIG. 3) the slope of nitrite accumulation is slightly steeper compared to the fermentation where nitrate was not added from the beginning (FIG. 2). Therefore, it was decided to use a batch medium where no nitrate is added from the beginning as it is anyway not reduced by *Staphylococcus vitulinus* until the aeration is reduced.

Example 3

Mortadella Type Sausage Application Trial

To test the effect of the newly developed 2-phase fermentation procedure in an application test, 2 different fermentations were carried out; one fermentation of *Staphylococcus vitulinus* strain CHCC10896 following the standard fermentation and one fermentation following a 2-phase procedure as described above.

The cells of both fermentations were harvested and freeze-dried by adding a cryo additive. Both batches were used in an application context by producing 3 batches of emulsified sausages, 1 batch with *Staphylococcus vitulinus* fermented by the standard procedure, 1 batch with *Staphylococcus vitulinus* fermented by a 2-phase fermentation with nitrate feeding in the second phase and 1 batch with the commercial culture Bactoferm® CS-300 (Chr. Hansen, Denmark) composed of 2 *carnosus* strains which served as a control.

Experimental

Cell Count Determination of Freeze-Dried Granulate.

The cell count determination was carried out by flowcytometry:

| Strain | Sample ID | Active/g | CV | Total/g | CV | Active/total | SD |
|---|---|---|---|---|---|---|---|
| S. vitulinus | Std | 5.97E+11 | 3.9% | 9.97E+11 | 2.0% | 60% | 1.1% |
| S. vitulinus | Nitrate feed | 4.95E+11 | 0.2% | 5.54E+11 | 0.5% | 89% | 0.3% |

CV: Coefficient of variation.
SD: Standard deviation.

Emulsified Sausage

Mortadella type sausage—recipe (10 kg batch):

| | | |
|---|---|---|
| 20% | RII (lean beef) | 2 kg |
| 40% | SII (pork shoulder) | 4 kg |
| 20% | Fat (pork fat) | 2 kg |
| 20% | Ice | 2 kg |
| 20 g/kg | Common salt | 200 g |
| 2 g/kg | White pepper | 20 g |
| 0.5 g/kg | Cardamom | 5 g |
| 2 g/kg | Dextrose | 20 g |
| 3 g/kg | Di-phosphate | 30 g |
| 0.1 g/kg | Na-nitrate | 1 g |

All meat and fat were grinded through a 2 mm plate
All ingredients including bacterial cultures were put in a bowl (Mado Supra 35), chopped and cut at 4000 rpm and bowl speed 2
10 rounds followed by cleaning and addition of 500 g $CO_2$ (lower chopping temperature)
20 rounds (30 in total) followed by cleaning
20 rounds (50 in total) to finish cutting
The blend was stuffed into 75 mm Nalo TOP casings (+8 cups for analyses)
The curing treatment was carried out at 4° C., 12° C. and 18° C. for 21 hours
Heat treatment at 80° C. in chamber until 72° C. in the center
20 minutes cold shower
Left in chilling room at 4° C. for 24 hrs Target Cell Count/Inoculation Level As CS-300 was used as control, both *Staphylococcus vitulinus* samples were dosed according to the target cell count of CS-300 for 100 kg of meat. Originally, both strains in CS-300 were dosed at the same level but due to the switch of the MIII fermentation medium, this strain was overdosed by 20% as safety margin:

Target cell count of CS-300=3.2×10$^{12}$ CFU/100kg

A safety margin of 20% was added on every product onto target cell count.

Target cell count of *Staphylococcus vitulinus* samples=3.0×10$^{12}$ CFU/100kg of meat+20% safety margin

*Staphylococcus vitulinus*—standard (1)=6.03 g/100 kg
*Staphylococcus vitulinus*—nitrate feed (2)=7.27 g/100 kg Naming of Batches
1) *Staphylococcus vitulinus*—standard
2) *Staphylococcus vitulinus*—nitrate feed
3) Bactoferm® CS-300

Incubation/Fermentation

In each case 3 sausages of each of the three batches were fermented at the following temperatures for 21 hours before cooking to mimic the tumbling process:
4° C.
12° C.
18° C.

Results

Chemical Analysis

Figure 4:
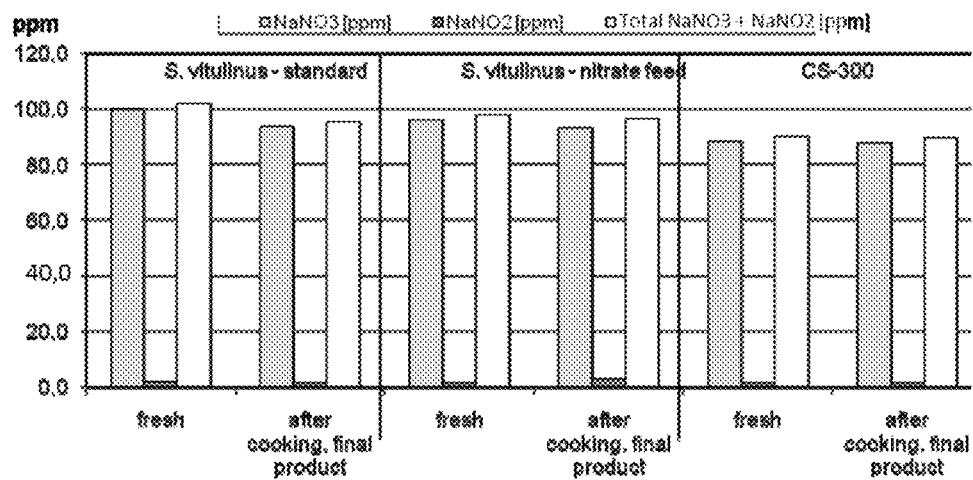
FIG. 4 shows the nitrate/nitrite concentrations in mortadella-type sausages fermented at 4° C. for 21 hours before cooking with *Staphylococcus vitulinus* strain CHCC10896 produced by standard fermentation (*S. vitulinus*—standard), *Staphylococcus vitulinus* strain CHCC10896 produced by two-phase fermentation (*S. vitulinus*—nitrate feed), or Bactoferm® CS-300 (CS-300).
Figure 5:
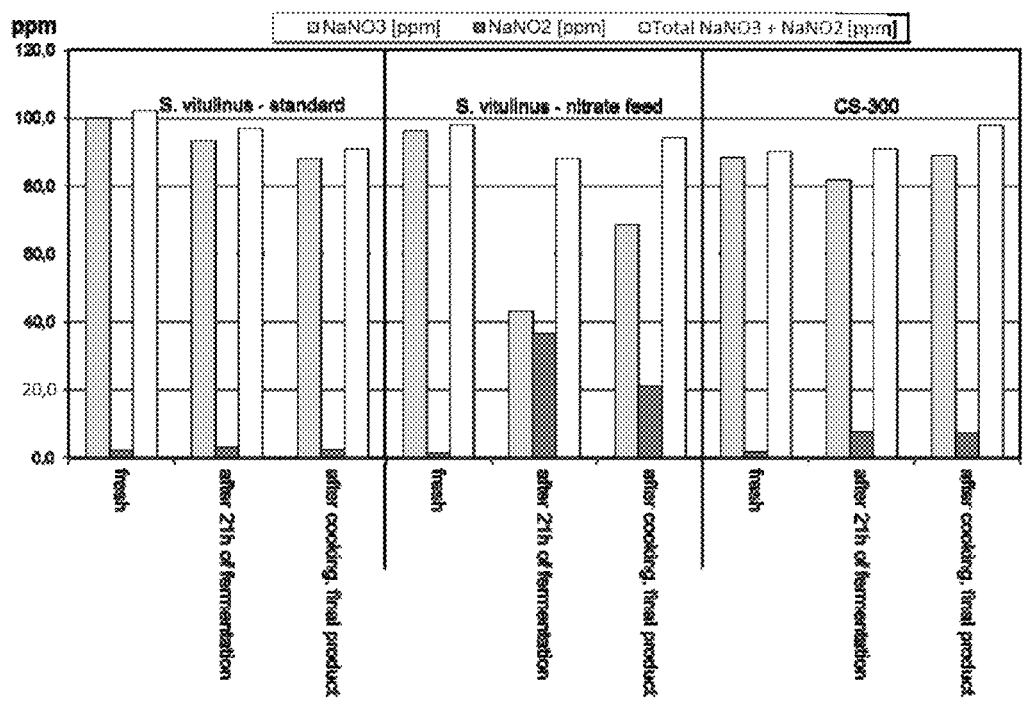
FIG. 5 shows the nitrate/nitrite concentrations in mortadella-type sausages fermented at 12° C. for 21 hours before cooking with *Staphylococcus vitulinus* strain CHCC10896 produced by standard fermentation (*S. vitulinus*—standard), *Staphylococcus vitulinus* strain CHCC10896 produced by two-phase fermentation (*S. vitulinus*—nitrate feed), or Bactoferm® CS-300 (CS-300).
Figure 6:
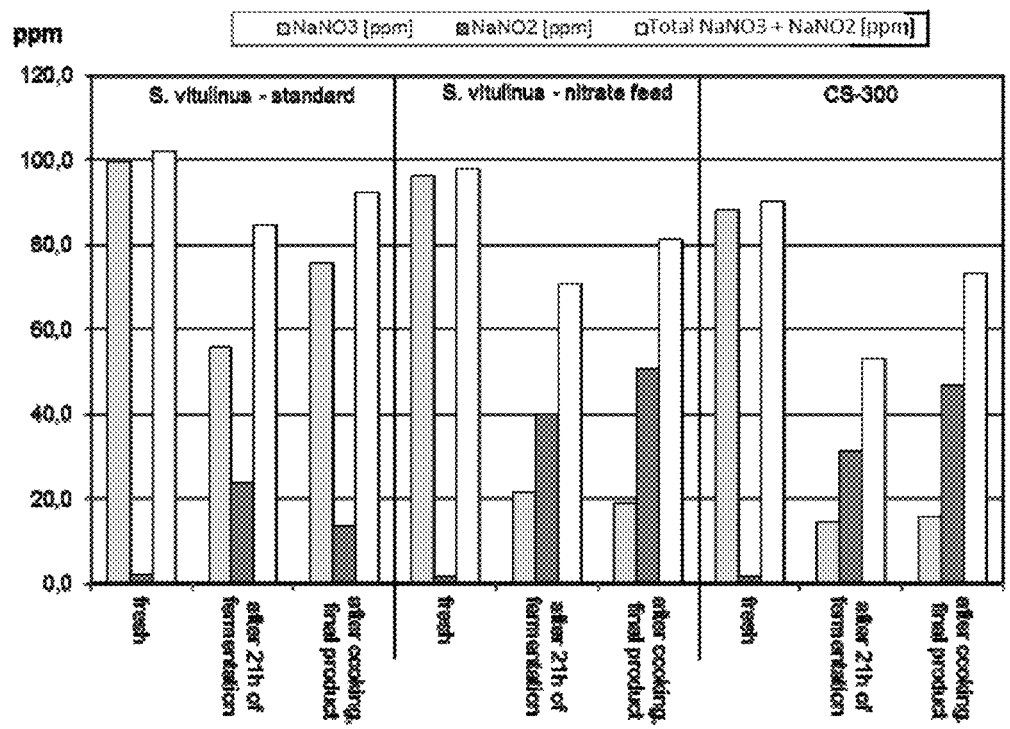
FIG. 6 shows the nitrate/nitrite concentrations in mortadella-type sausages fermented at 18° C. for 21 hours before cooking with *Staphylococcus vitulinus* strain CHCC10896 produced by standard fermentation (*S. vitulinus*—standard), *Staphylococcus vitulinus* strain CHCC10896 produced by two-phase fermentation (*S. vitulinus*—nitrate feed), or Bactoferm® CS-300 (CS-300).

Nitrate/nitrite concentrations on raw material before stuffing, on raw material after 21 of fermentation and on final product after cooking were determined by the method described above (FIGS. 4-6).

Microbiological Analysis

Raw material taken out after fermentation and before cooking.

| | |
|---|---|
| 1) - 4° C. | 5.0 × 10$^6$ CFU/g |
| 2) - 4° C. | 3.9 × 10$^7$ CFU/g |
| 3) - 4° C. | 4.4 × 10$^7$ CFU/g |
| 1) - 12° C. | 8.2 × 10$^6$ CFU/g |
| 2) - 12° C. | 4.7 × 10$^7$ CFU/g |
| 3) - 12° C. | 4.2 × 10$^7$ CFU/g |
| 1) - 18° C. | 7.6 × 10$^6$ CFU/g |
| 2) - 18° C. | 5.9 × 10$^7$ CFU/g |
| 3) - 18° C. | 5.1 × 10$^7$ CFU/g |

Determination of Red Color Intensity

Figure 7:
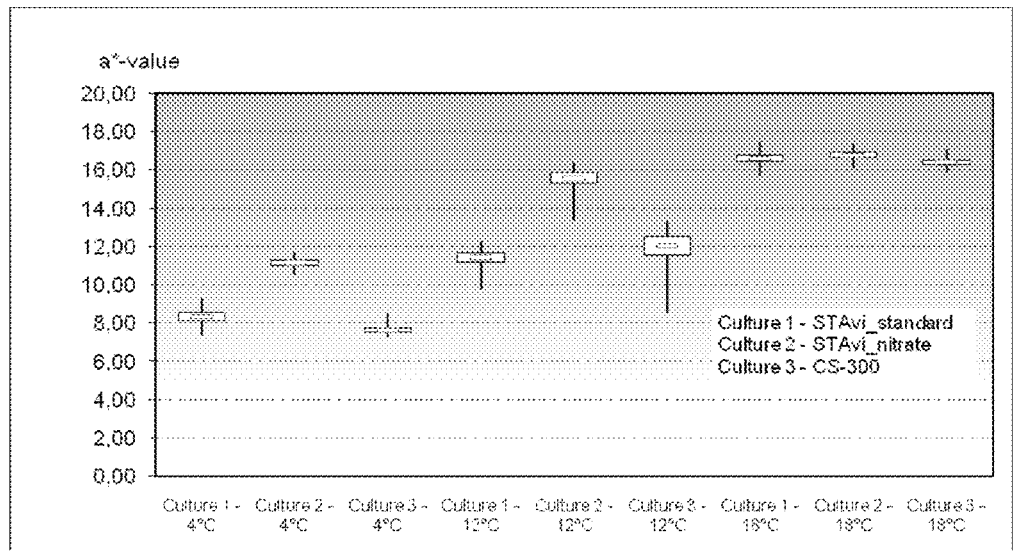
FIG. 7 depicts the red color intensity (a*-value according to the L*a*b*-system) of mortadella-type sausages fermented for 21 hours at 4° C., 12° C. or 18° C. before cooking with *Staphylococcus vitulinus* strain CHCC10896 produced by standard fermentation (STAvi_standard), *Staphylococcus vitulinus* strain CHCC10896 produced by two-phase fermentation (STAvi_nitrate), or Bactoferm® CS-300 (CS-300).

Samples were measured in a Konica Minolta colorimeter and a* values were determined according to the L*a*b* color system (FIG. 7).

Discussion

It could be clearly shown that the modification of the fermentation procedure of *Staphylococcus vitulinus* strain CHCC10896 leads to a significant improvement of nitrate reductase activity in meat application. The strain produced by a nitrate feeding during oxygen limited growth phase leads to a nice reddening even at low temperatures which is reflected by the results of the nitrate/nitrite determination and the red color intensity determination. There is a clear advantage of a nitrate feeding during oxygen limited phase compared to the standard fermentation process. A significant difference can be seen on the red color intensity especially at low temperatures (4° C. and 12° C.). Furthermore, it is shown that *Staphylococcus vitulinus* strain CHCC10896 produced by nitrate feeding shows a reddening performance significantly better than CS-300 at 4° C. and 12° C.

Example 4

Second Mortadella Type Sausage Application Trial

To confirm the results of the first and second application trial, another application trial with newly produced freeze-dried material was performed to ensure the robustness of the 2-step fermentation procedure.

4 different batches of emulsified sausage were produced by applying *Staphylococcus vitulinus* produced by a 2-step fermentation procedure either with or without added nitrate from the beginning, CS-300 and NatuRed LT. The sausages were incubated at different temperatures (4° C., 8° C., and 12° C.) and fermentation at these temperatures were carried out for 7 hours, 12 hours and 24 hours to follow the development of nitrate reduction and reddening process.

Experimental

Cell Count Determination of Freeze-Dried Granulate Produced as Described in Example 2

The cell count determination was carried out by flowcytometry:

| Strain | Sample ID | Active/g | CV | Total/g | CV | Active/total |
|---|---|---|---|---|---|---|
| S. vitulinus | Nitrate feed, Nitrate from beginning | 4.17E+11 | 9.8% | 5.54E+11 | 2.3% | 75% |
| S. vitulinus | Nitrate feed, no nitrate form beginning | 4.23E+11 | 3.1% | 5.18E+11 | 1.1% | 82% |

CV: Coefficient of variation.
SD: Standard deviation.

Emulsified Sausage

Mortadella type sausage—recipe (15 kg batch):

| | | |
|---|---|---|
| 20% | RII (lean beef) | 3 kg |
| 40% | SII (pork shoulder) | 6 kg |
| 20% | Fat (pork fat) | 3 kg |

| | | |
|---|---|---|
| 20% | Ice | 3 kg |
| 20 g/kg | Common salt | 300 g |
| 2 g/kg | White pepper | 30 g |
| 0.5 g/kg | Cardamom | 7.5 g |
| 2 g/kg | Dextrose | 30 g |
| 3 g/kg | Di-phosphate | 45 g |
| 0.1 g/kg | Na-nitrate | 1.5 g |

Figure 8:
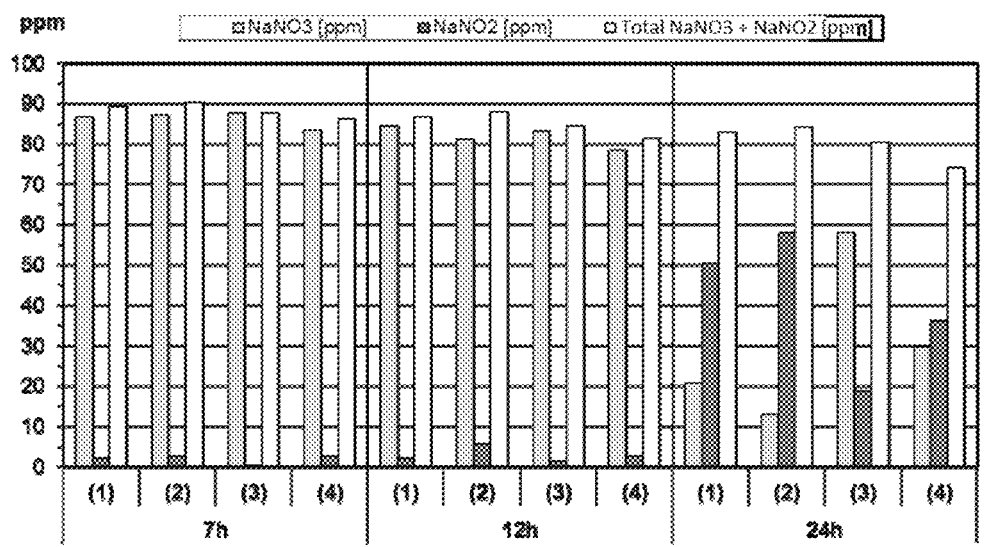
FIG. 8 shows the nitrate and nitrite concentration of mortadella-type sausage mince before cooking after different incubation intervals (7, 12 and 24 hours) at 4° C. with *Staphylococcus vitulinus* strain CHCC10896 produced by two-phase fermentation, nitrate from beginning (1), *Staphylococcus vitulinus* strain CHCC10896 produced by two-phase fermentation, no nitrate from beginning (2), Bactoferm® CS-300 (3) or TEXEL® NatuRed LT (4).
Figure 9:
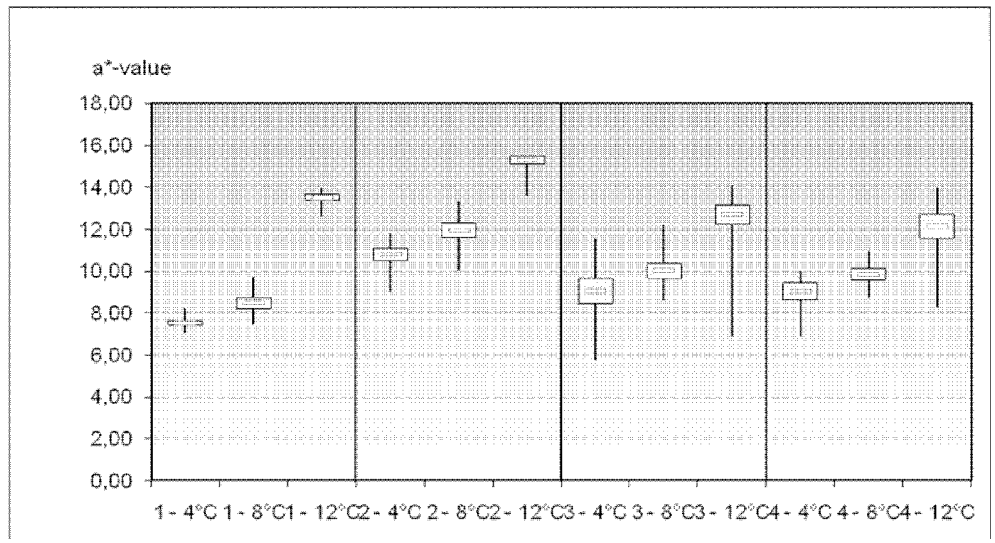
FIG. 9 depicts the red color intensity (a*-value according to the L*a*b*-system) of mortadella-type sausages fermented for 7 hours at 4° C., 8° C. or 12° C. before cooking with *Staphylococcus vitulinus* strain CHCC10896 produced by two-phase fermentation, nitrate from beginning (1), *Staphylococcus vitulinus* strain CHCC10896 produced by two-phase fermentation, no nitrate from beginning (2), Bactoferm® CS-300 (3) or TEXEL® NatuRed LT (4).
Figure 10:
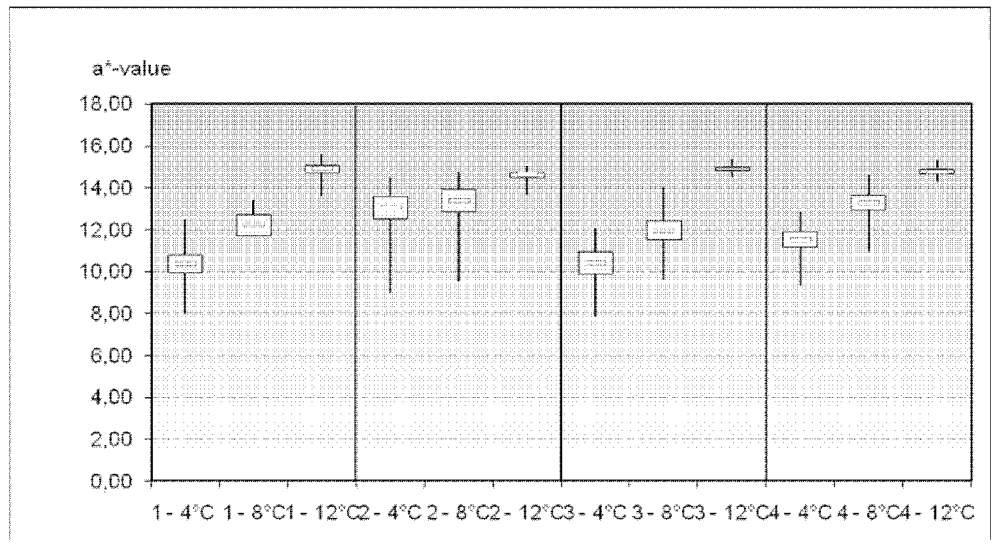
FIG. 10 depicts the red color intensity (a*-value according to the L*a*b*-system) of mortadella-type sausages fermented for 12 hours at 4° C., 8° C. or 12° C. before cooking with *Staphylococcus vitulinus* strain CHCC10896 produced by two-phase fermentation, nitrate from beginning (1), *Staphylococcus vitulinus* strain CHCC10896 produced by two-phase fermentation, no nitrate from beginning (2), Bactoferm® CS-300 (3) or TEXEL® NatuRed LT (4).
Figure 11:
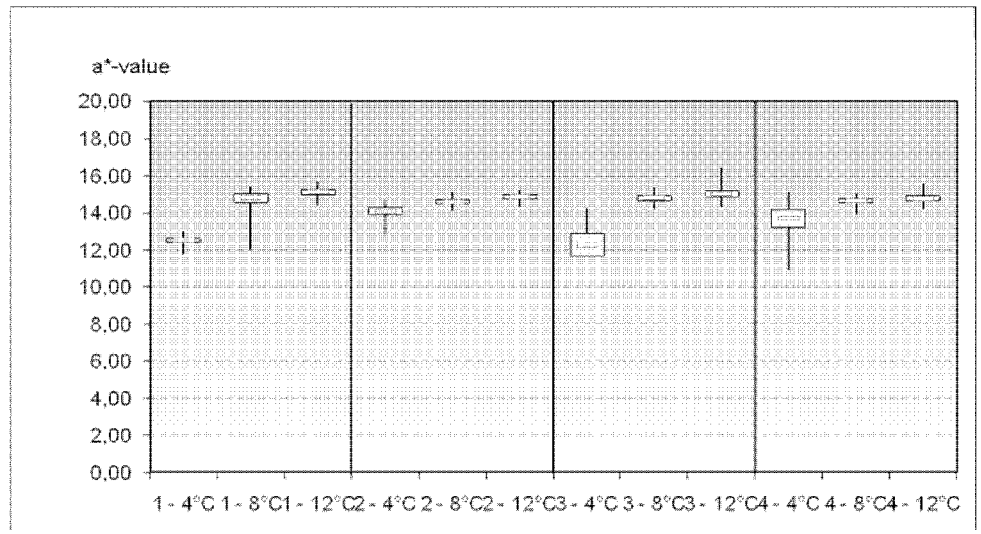
FIG. 11 depicts the red color intensity (a*-value according to the L*a*b*-system) of mortadella-type sausages fermented for 24 hours at 4° C., 8° C. or 12° C. before cooking with *Staphylococcus vitulinus* strain CHCC10896 produced by two-phase fermentation, nitrate from beginning (1), *Staphylococcus vitulinus* strain CHCC10896 produced by two-phase fermentation, no nitrate from beginning (2), Bactoferm® CS-300 (3) or TEXEL® NatuRed LT (4).

All meat and fat were grinded through a 2 mm plate
All ingredients including bacterial cultures were put in a bowl (Mado Supra 35), chopped and cut at 4000 rpm and bowl speed 2
10 rounds followed by cleaning and addition of 500 g $CO_2$ (lower chopping temperature)
20 rounds (30 in total) followed by cleaning
30 rounds (60 in total) to finish cutting
The blend was divided into 3 batches of 5 kg
Cutting further 15 rounds at 2000 rpm and bowl speed 1
The blend was stuffed into 75 mm Nalo TOP casings (+cups for analyses)
The curing treatment was carried out at 4° C., 8° C. and 12° C. for 24 hours
Heat treatment at 80° C. in chamber until 72° C. in the center
20 minutes cold shower
Left in chilling room at 4° C. for 24 hrs.
Target Cell Count/Inoculation Level
Target cell count for *Staphylococcus vitulinus* strain CHCC10896 as mentioned before is $3.0 \times 10^{12}$ CFU/100 kg of meat. Bactoferm® CS-300 and TEXEL® NaturRed LT were applied as recommended by the product information.
Naming of Batches
  1) *Staphylococcus vitulinus*—nitrate feed; nitrate from the beginning
  2) *Staphylococcus vitulinus*—nitrate feed; no nitrate from the beginning
  3) Bactoferm® CS-300
  4) TEXEL® NatuRed LT
Incubation/Fermentation
  In each case 4 sausages of each of the four batches were fermented at the following temperatures to mimic the tumbling process:
    4° C.
    12° C.
    18° C.
Incubation Time Before Cooking
  7 hours
  12 hours
  24 hours
Results
Chemical Analysis
  For each culture, incubation time and temperature prior to cooking
    A total of 36 samples (red cap beakers) were analyzed For each culture, incubation time and temperature after cooking
    A total of 36 samples (final sausages) were analyzed FIG. 8.
Determination of Red Color Intensity
  Samples were measured in a Konica Minolta colorimeter and a* values were determined according to the L*a*b* color system (FIGS. 9-11)
Discussion
  The data confirm the results of the previous trials (Example 3 and 4). *Staphylococcus vitulinus* strain CHCC10896 shows a more effective nitrate to nitrite conversion at all tested temperatures compared Bactoferm® CS-300 and is at least comparable to TEXEL® NatuRed. The better nitrate to nitrite conversion is also documented by the more intensive red color of sausages produced by *Staphylococcus vitulinus* strain CHCC10896. However, the presence of nitrate in the batch medium from the beginning of the fermentation seems to have a negative influence on nitrate conversion and red color formation as this batch seems to be less efficient compared to the batch where no nitrate was present until the feeding was started. The trial shows a clear advantage of *Staphylococcus vitulinus* strain CHCC10896 produced by a 2-step fermentation process, a first aerobic phase without the presence of nitrate in the batch medium and a second anaerobic or oxygen limited phase with a continuous feed of nitrate.

Example 5

Cooked Ham Application Trial

*Staphylococcus vitulinus* strain CHCC10896 was tested in a cooked ham model compared to Bactoferm® CS-299 (Chr. Hansen, Denmark), the culture which is most commonly used for this application area besides Bactoferm® CS-300. Bactoferm® CS-299 is composed of only one *Staphylococcus carnosus* strain whereas Bactoferm® CS-300 is composed of two different *Staphylococcus carnosus* strains. The cell count of Bactoferm® CS-300 is twice the cell count of Bactoferm® CS-299.
Experimental
  Production of cooked ham by applying *Staphylococcus vitulinus* strain CHCC10896 produced by a 2-phase fermentation procedure in comparison to Bactoferm® CS-299. The inoculation level of *Staphylococcus vitulinus* strain CHCC10896 was aligned to the target cell count of Bactoferm® CS-299 ($1.5 \times 10^{12}$ CFU/kg).
Cooked Ham
  1. Cutting round muscle of pork leg (nut) in order to get lean meat.
  2. "Crushing" the meat by grinder (Mado MEW 718) running with auger only.
  3. Bacterial culture and brine was added to the meat. Tumbling by tumbling machine (Rühle MKR 150) for 16 hours at 6° C. Total rounds 5220. 15 minutes running by 10 rpm and 15 minutes rest.
  4. Packing vacuum in PE/PA bags.
  5. Molding.
  6. Heat treatment in Autotherm camber by steam at 80° C. until 75° C. in centre, followed by 10 minutes cold shower.
  7. Final chilling at 3-4° C. in chilling room.
  8. De-molding and cutting.
  100 kg meat plus 15 kg brine (15%)

| | |
|---|---|
| Brine calculation in order to achieve: | 0.2% dextrose |
| 2% common salt in end product | 0.3% di-phosphate |
| (115 kg, no weight loss) | 0.01% potassium nitrate |
| Meat | 8000 g |
| Common salt | 184 g |
| Dextrose | 18 g |
| Di-phospate | 28 g |
| Potassium nitrate | 1 g |
| Tap water | 969 g |
| Culture | see above |
| Total | 9200 g |

Results
Determination of Red Color Intensity

Due to the fact that a cooked ham normally does not have a homogenous surface a 0.5 cm slice of each batch was homogenized by grinding. The grinded material of each batch was layered into a Petri dish which gives a homogenous surface for red color determination.

Figure 12:
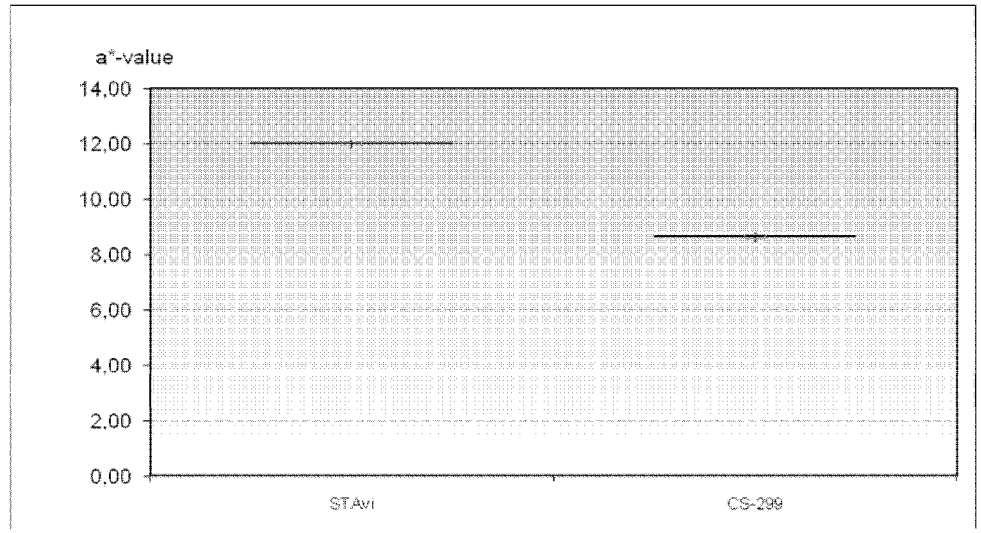
FIG. 12 depicts the red color intensity (a*-value according to the L*a*b*-system) of cooked ham fermented for 16 hours at 6° C. with *Staphylococcus vitulinus* strain CHCC10896 produced by two-phase fermentation, no nitrate from beginning (STAvi) or Bactoferm® CS-299 (CS-299).

Samples were measured in a Konica Minolta colorimeter CR-400 and a* values were determined according to the L*a*b* color system (FIG. 12).

Figure 13:
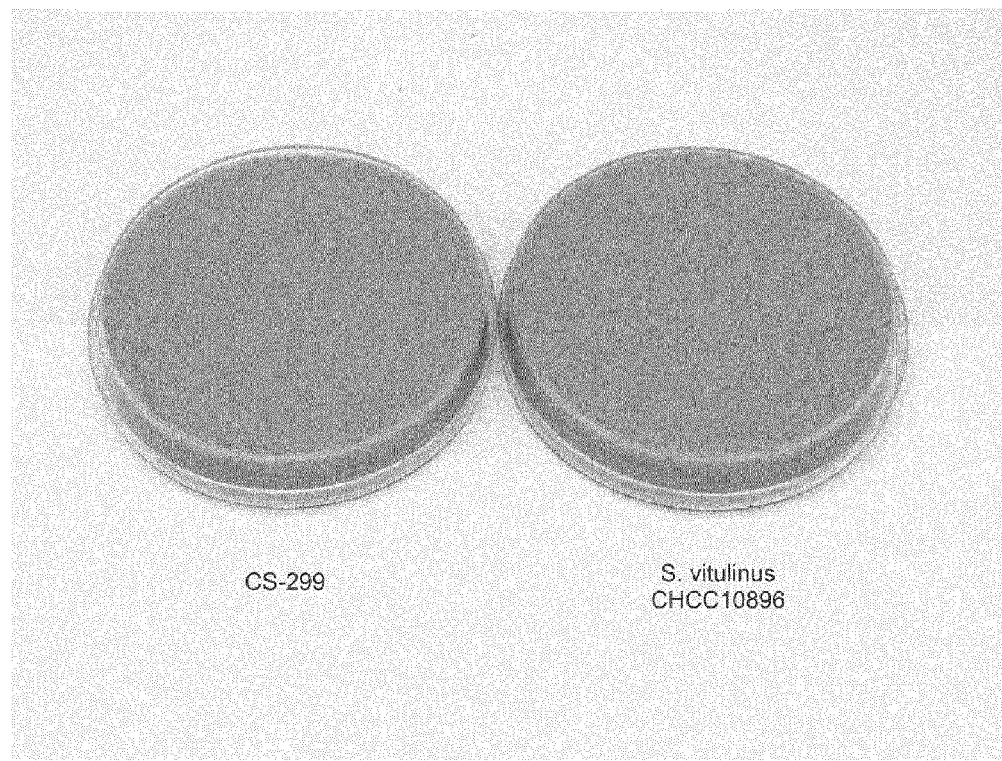
FIG. 13 shows petri dishes with grinded cooked ham fermented with Bactoferm® CS-299 (CS-299) or *Staphylococcus vitulinus* strain CHCC10896 produced by two-phase fermentation, no nitrate from beginning (*S. vitulinus* CHCC10896).

Furthermore, the red color intensity was examined visually (FIG. 13).

Discussion

From visual observation and red color intensity determination it can be concluded that *Staphylococcus vitulinus* strain CHCC10896 produced by using a 2-step fermentation procedure gives a better color than Bactoferm® CS-299 when tumbled at low temperatures (6° C.): The cooked ham prepared with *Staphylococcus vitulinus* strain CHCC10896 pre-treated with the two-phase fermentation method had a more intense and brighter red color than the cooked ham prepared with Bactoferm® CS-299 (FIG. 13). This could also be measured as a higher a*-value (red color intensity) according to the L*a*b*-system of the cooked ham prepared with *Staphylococcus vitulinus* strain CHCC10896 pre-treated with the two-phase fermentation method (FIG. 12). The more intense red color is most probably due to a more efficient conversion/reduction of nitrate to nitrite.

Example 6

*Staphylococcus vitulinus* Strain CHCC11576 Fermented According to the Standard Fermentation Procedure Compared to the 2-Phase Fermentation Procedure in an Emulsified Sausage Application To test if the 2-phase fermentation procedure is also improving the ability of a different *Staphylococcus vitulinus* strain to convert metmyoglobin into nitrosylmyoglobin to produce a stable red color at low temperatures, the *Staphylococcus vitulinus* strain CHCC11576 was fermented according to the standard fermentation procedure and according to the 2-phase fermentation procedure as described before. The cells of both fermentations were harvested and freeze-dried. Both batches were used in an application test by producing 3 batches of emulsified sausages; 1 batch with *Staphylococcus vitulinus* strain CHCC11576 fermented by the standard procedure, 1 batch with *Staphylococcus vitulinus* strain CHCC11576 fermented by a 2-phase fermentation with nitrate feeding in the second phase, and 1 with a *Staphylococcus carnosus* strain A fermented by the standard procedure.

Experimental
Cell Count Determination of Freeze-Dried Granulate.

The cell count determination was carried out by flowcytometry:

Emulsified Sausage:
Mortadella Type Sausage—Recipe (5 kg Batch):
Mortadella Type:

| 20% | RII (lean beef) | 1 kg |
| 40% | SII (pork shoulder) | 2 kg |
| 20% | Fat (pork fat) | 1 kg |
| 20% | Ice | 1 kg |
| 2 g/kg | Dextrose | 10 g |
| 3 g/kg | Di-phosphate | 15 g |
| 0.1 g/kg | Na-nitrate | 0.5 g |

The mortadella type sausage was prepared according to the procedure described before.

Target Cell Count/Inoculation Level

Target cell count=3.2E12 CFU/100 kg (including 20% safety margin) Each batch was inoculated according to the same target cell count.

Naming of Batches
1) CHCC11576—standard
2) CHCC11576—nitrate feed
3) *S. carnosus*

Incubation/Fermentation

In each case 3 sausages of each of the three batches were fermented at the following temperatures for 20, respectively 18, hours before cooking to mimic the tumbling process of cooked ham:
4° C.
8° C.

Results
Determination of Red Color Intensity

Figure 14:
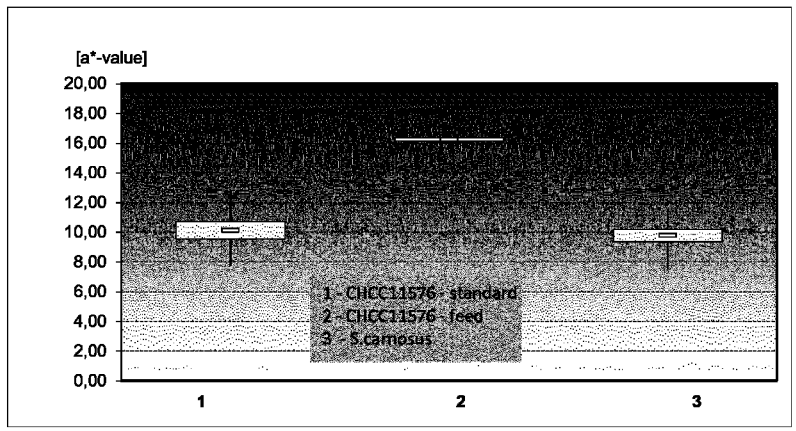
FIG. 14 depicts the red color intensity (a*-value according to the L*a*b*-system) of mortadella-type sausages fermented for 20 hours at 4° C. prior to cooking with *Staphylococcus vitulinus* strain CHCC111576 produced by standard fermentation (CHCC11576—standard), *Staphylococcus vitulinus* strain CHCC11576 produced by two-phase fermentation (CHCC11576—feed), or *Staphylococcus carnosus* strain A produced by standard fermentation (*S. carnosus*).
Figure 15:
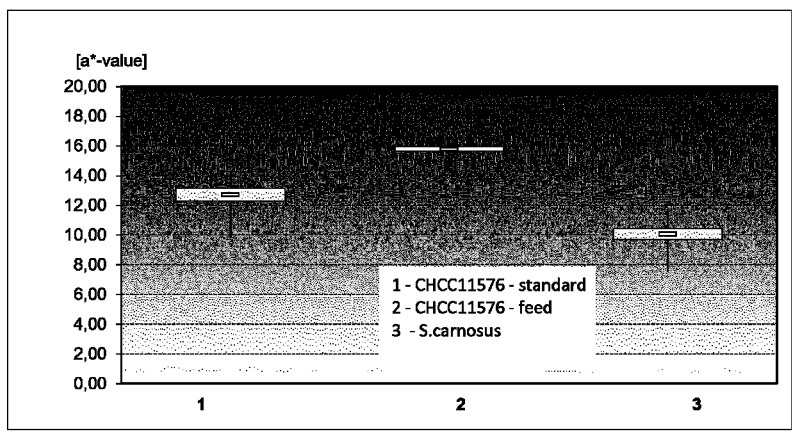
FIG. 15 depicts the red color intensity (a*-value according to the L*a*b*-system) of mortadella-type sausages fermented for 18 hours at 8° C. prior to cooking with *Staphylococcus vitulinus* strain CHCC111576 produced by standard fermentation (CHCC11576—standard), *Staphylococcus vitulinus* strain CHCC11576 produced by two-phase fermentation (CHCC11576—feed), or *Staphylococcus carnosus* strain A produced by standard fermentation (*S. carnosus*).
Figure 16:
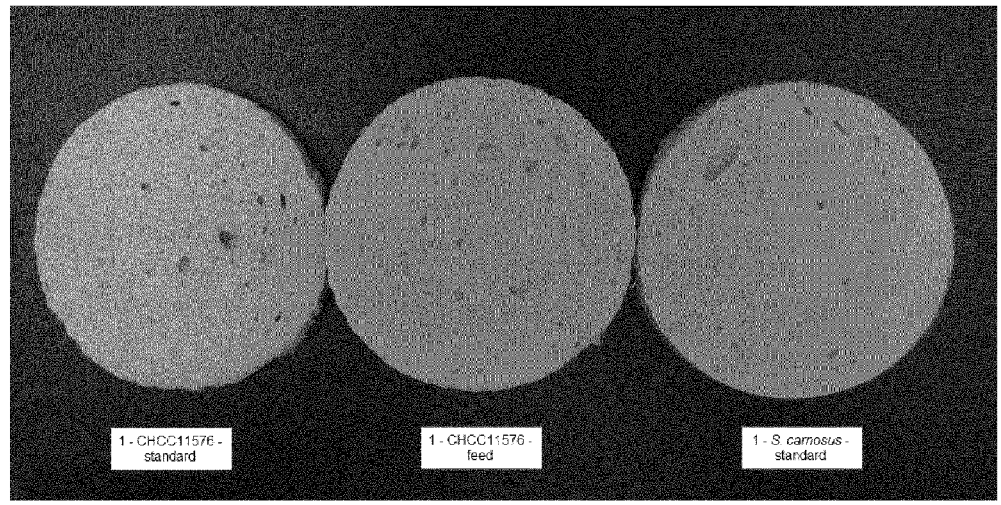
FIG. 16 shows mortadella-type sausages fermented for 20 hours at 4° C. prior to cooking with *Staphylococcus vitulinus* strain CHCC11576 produced by standard fermentation (CHCC11576—standard), *Staphylococcus vitulinus* strain CHCC11576 produced by two-phase fermentation (CHCC11576—feed), or *Staphylococcus carnosus* strain A produced by standard fermentation (*S. carnosus*—standard).
Figure 17:
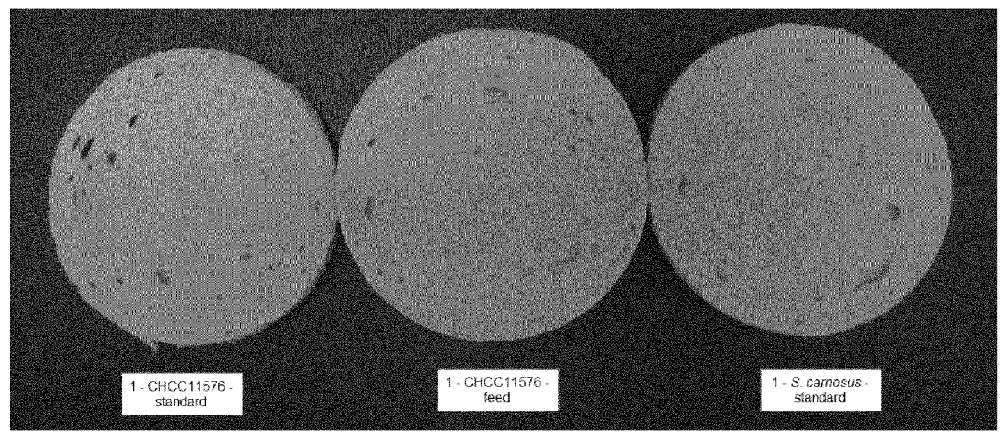
FIG. 17 shows mortadella-type sausages fermented for 18 hours at 8° C. prior to cooking with *Staphylococcus vitulinus* strain CHCC11576 produced by standard fermentation (CHCC11576—standard), *Staphylococcus vitulinus* strain CHCC11576 produced by two-phase fermentation (CHCC11576—feed), or *Staphylococcus carnosus* strain A produced by standard fermentation (*S. carnosus*—standard).

Samples were measured in a Konica Minolta colorimeter and a* values were determined according to the L*a*b* color system (FIGS. 14 and 15). Furthermore, the red color intensity was examined visually (FIGS. 16 and 17).

Figure 18:
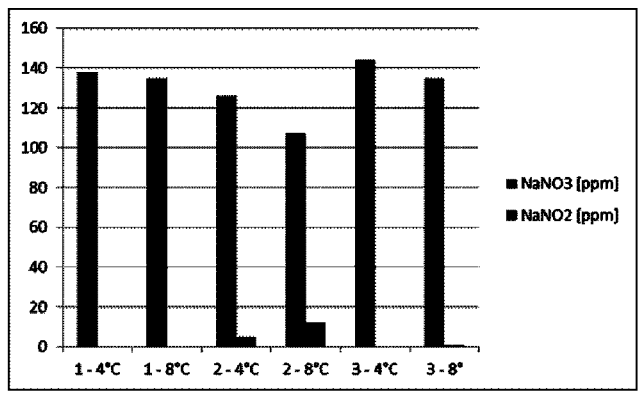
FIG. 18 depicts the nitrate/nitrite concentrations in mortadella-type sausages fermented at 4° C. for 20 hours (4° C.) or at 8° C. for 18 hours (8° C.) before cooking with *Staphylococcus vitulinus* strain CHCC11576 produced by standard fermentation (1), *Staphylococcus vitulinus* strain CHCC11576 produced by two-phase fermentation (2), or *Staphylococcus carnosus* strain A produced by standard fermentation (3).

Determination of Nitrate/Nitrite Concentration:

Samples of each batch were filled in red cap beakers and incubated at 4° C. and 8° C. together with the sausages for the same duration. The samples were stored at −20° C. directly after incubation (4° C.=20 h; 8° C.=18 h). The samples were analyzed with regard to nitrate/nitrite concentration enzymatically as described in Amtliche Sammlung von Untersuchungsverfahren §64 Lebensmittel-und Futtermittelgesetzbuch (LFGB; German Food and Feed Act) (L 07.00-60) and the results are depicted in FIG. 18.
1) *S. vitulinus* CHCC11576—standard
2) *S. vitulinus* CHCC11576—nitrate feed
3) *S. carnosus*

Conclusion:

It could clearly be shown, that the modification of the fermentation procedure of *Staphylococcus vitulinus* strain CHCC11576 leads to a significant improvement of nitrate reductase activity in meat application. The strain produced by a nitrate feeding during oxygen limited growth phase leads to a nice reddening at relatively low temperatures of 4° C. and 8° C. which is reflected by the red color intensity determination

| Strain | Batch | Active/g | CV | Total/g | CV | Active/Total | SD |
|---|---|---|---|---|---|---|---|
| *S. vitulinus* CHCC11576 | Standard fermentation | 8.65E+11 | 0.7% | 1.18E+12 | 1.5% | 74% | 0.5% |
| *S. vitulinus* CHCC11576 | 2-phase fermentation | 3.47E+11 | 1.8% | 4.52E+11 | 1.2% | 77% | 0.4% |

CV: Coefficient of variation.
SD: Standard deviation.

which shows an a*-value (red color intensity) according to the L*a*b*-system significantly higher than the a*-value measured for the sausage prepared using either *Staphylococcus vitulinus* CHCC11576 produced by standard fermentation or *Staphylococcus* strain A produced by standard fermentation (FIGS. 14 and 15) and the photographic documentation showing a more red coloration of the sausage prepared with *Staphylococcus vitulinus* CHCC11576 produced by the two-phase fermentation method of the invention (FIGS. 16 and 17). Furthermore, it could be shown, that more nitrate is reduced and more nitrite is developed by *Staphylococcus vitulinus* CHCC11576 when fermented according to the two-phase fermentation procedure by feeding nitrate during the anaerobic phase (Figure FIG. 18). In the case of *Staphylococcus vitulinus* CHCC111576 when subjected to standard fermentation no nitrite could be detected within the meat samples and the nitrate concentration is significantly higher. There is a clear advantage of a nitrate feeding during oxygen limited phase compared to the standard fermentation process. The improvement of *Staphylococcus vitulinus* CHCC11576 is comparable to the improvement already shown for *Staphylococcus vitulinus* CHCC10896, so that it can be concluded, that the optimization of the nitrate reductase activity by a 2-phase fermentation as described before is not exclusive for *Staphylococcus vitulinus* CHCC10896 but also for a different strain, in this case the strain *Staphylococcus vitulinus* CHCC11576. It is most likely, that the one can also reach an improvement of nitrate reductase activity for other species of the genus *Staphylococcus*, such as *Staphylococcus carnosus*.

Example 7

Comparison of Feed Fermentation and Spike Fermentation

Two fermentations were performed, testing if a continuous feeding during the second, low aerated phase of the fermentation is needed, or if giving only one high concentrated nitrate spike at the beginning of the second phase is as efficient in improving the nitrate reductase activity respectively the ability to convert metmyoglobin efficiently into nitrosylmyoglobin.

The two-phase fermentation ran aerobically until the dissolved oxygen level reached 0% (pO2=0). At this point the aeration was turned down from 6 to 1 L/min and the nitrate feeding was started (approx. 1 g/L*h—given in pulsed feeds every 10 min). The feeding was continued until all carbon source glycerol in the medium had been consumed (base stop).

The spike fermentation was fully aerated until base stop. At base stop (EFT: 10 h), the aeration was turned down to 1 L/min and the spike (containing approx. 72 g/L glycerol and 216 g/L potassium nitrate, which equates 3 g/L glycerol and 9 g/L nitrate in the fermenter) was added to the medium (Volume of spike was 500 mL). Glycerol was given with the nitrate spike, as nitrate is not reduced into nitrite if no carbon source is available.

Experimental

Cell Count Determination of Freeze-Dried Granulate.

The cell count determination was carried out by flowcytometry:

Emulsified Sausage:
Mortadella Type Sausage—Recipe (5 kg Batch):
Mortadella Type:

| 20%      | RII (lean beef)    | 1 kg   |
|----------|--------------------|--------|
| 40%      | SII (pork shoulder)| 2 kg   |
| 20%      | Fat (pork fat)     | 1 kg   |
| 20%      | Ice                | 1 kg   |
| 2 g/kg   | Dextrose           | 10 g   |
| 3 g/kg   | Di-phosphate       | 15 g   |
| 0.1 g/kg | Na-nitrate         | 0.5 g  |

The mortadella-type sausage was prepared according to the procedure described before.

Target Cell Count/Inoculation Level

Target cell count=3.2E12 CFU/100 kg (including 20% safety margin) Each batch was inoculated according to the same target cell count.

Naming of Batches
1) CHCC10896—spike
2) CHCC10896—feed
3) *S. carnosus*

Incubation/Fermentation

In each case 3 sausages of each of the three batches were fermented at the following temperatures for 20, respectively 18, hours before cooking to mimic the tumbling process of cooked ham:
 4° C.
 8° C.

Results

Determination of Red Color Intensity

Figure 19:
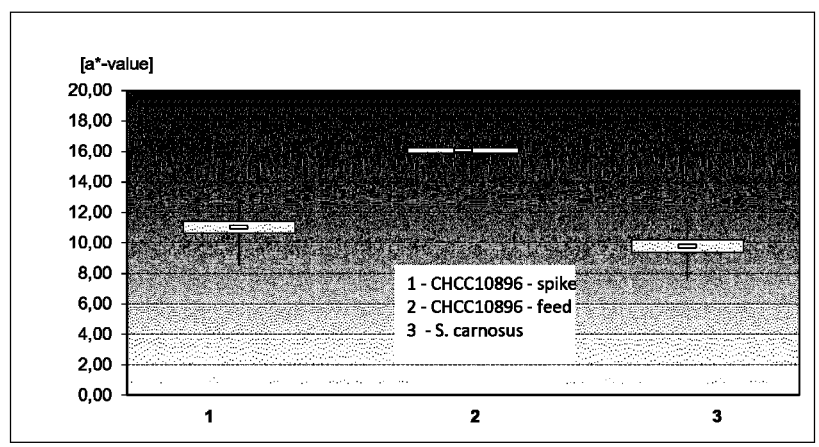
FIG. 19 depicts the red color intensity (a*-value according to the L*a*b*-system) of mortadella-type sausages fermented for 20 hours at 4° C. prior to cooking with *Staphylococcus vitulinus* strain CHCC10896 produced by two-phase fermentation giving only one high concentrated nitrate spike at the beginning of the second phase (CHCC10896—spike), *Staphylococcus vitulinus* strain CHCC10896 produced by two-phase fermentation with continuous nitrate feeding during the second phase (CHCC10896—feed), or *Staphylococcus carnosus* strain A produced by standard fermentation (*S. carnosus*).
Figure 20:
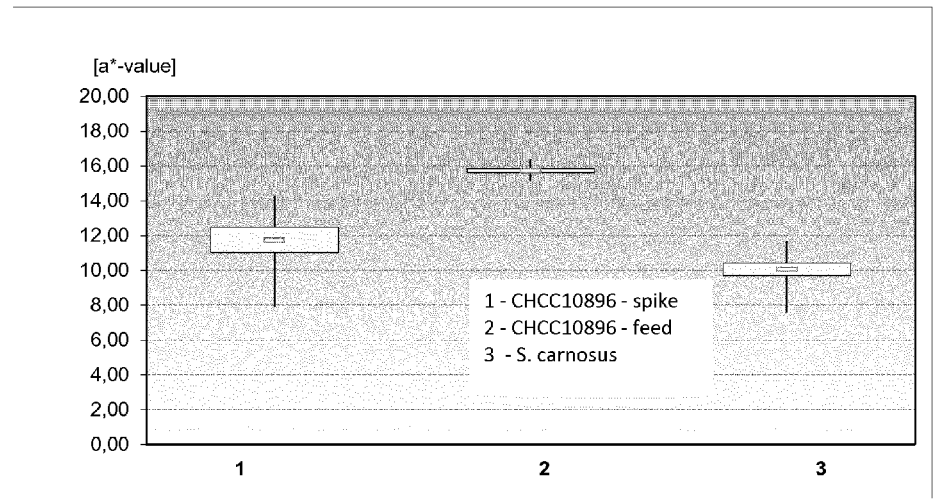
FIG. 20 depicts the red color intensity (a*-value according to the L*a*b*-system) of mortadella-type sausages fermented for 18 hours at 8° C. prior to cooking with *Staphylococcus vitulinus* strain CHCC10896 produced by two-phase fermentation giving only one high concentrated nitrate spike at the beginning of the second phase (CHCC10896—spike), *Staphylococcus vitulinus* strain CHCC10896 produced by two-phase fermentation with continuous nitrate feeding during the second phase (CHCC10896—feed), or *Staphylococcus carnosus* strain A produced by standard fermentation (*S. carnosus*).

Samples were measured in a Konica Minolta colorimeter and a* values were determined according to the L*a*b* color system (FIGS. 19 and 20).

Figure 21:
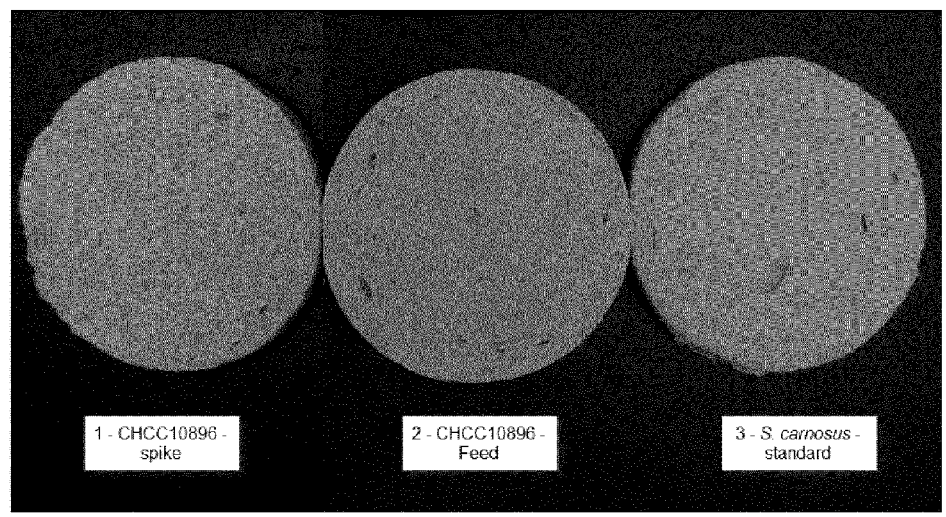
FIG. 21 shows mortadella-type sausages fermented for 20 hours at 4° C. prior to cooking with *Staphylococcus vitulinus* strain CHCC10896 produced by two-phase fermentation giving only one high concentrated nitrate spike at the beginning of the second phase (CHCC10896—spike), *Staphylococcus vitulinus* strain CHCC10896 produced by two-phase fermentation with continuous nitrate feeding during the second phase (CHCC10896—feed), or *Staphylococcus carnosus* strain A produced by standard fermentation (*S. carnosus*—standard).
Figure 22:
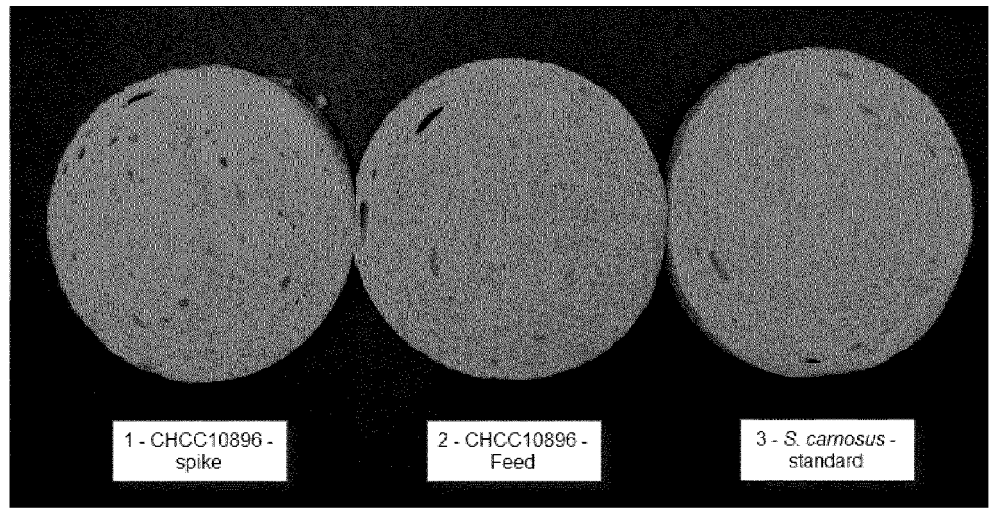
FIG. 22 shows mortadella-type sausages fermented for 18 hours at 8° C. prior to cooking with *Staphylococcus vitulinus* strain CHCC10896 produced by two-phase fermentation giving only one high concentrated nitrate spike at the beginning of the second phase (CHCC10896—spike), *Staphylococcus vitulinus* strain CHCC10896 produced by two-phase fermentation with continuous nitrate feeding during the second phase (CHCC10896—feed), or *Staphylococcus carnosus* strain A produced by standard fermentation (*S. carnosus*—standard).

Furthermore, the red color intensity was examined visually (FIGS. 21 and 22).

Figure 23:
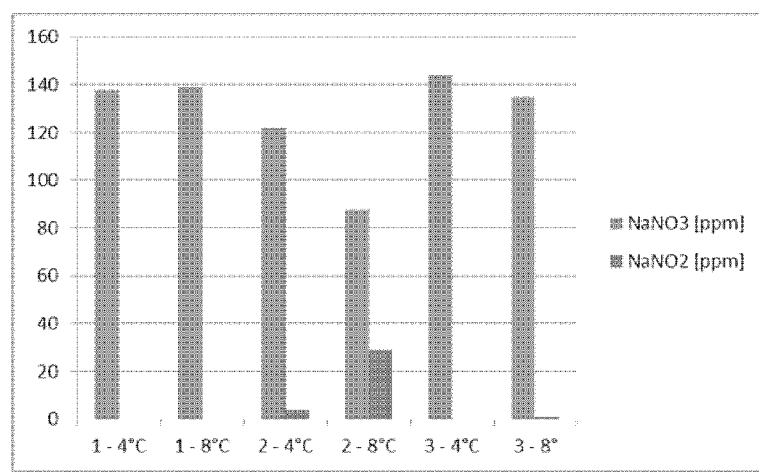
FIG. 23 depicts the nitrate/nitrite concentrations in mortadella-type sausages fermented at 4° C. for 20 hours (4° C.) or at 8° C. for 18 hours (8° C.) before cooking with *Staphylococcus vitulinus* strain CHCC110896 produced by two-phase fermentation giving only one high concentrated nitrate spike at the beginning of the second phase (1), *Staphylococcus vitulinus* strain CHCC10896 produced by two-phase fermentation with continuous feeding of nitrate during the second phase (2), or *Staphylococcus carnosus* strain A produced by standard fermentation (3).

Determination of Nitrate/Nitrite Concentration:

Samples of each batch were filled in red cap beakers and incubated at 4° C. and 8° C. together with the sausages for the same duration. The samples were stored at −20° C. directly after incubation (4° C.=20 h; 8° C.=18 h). The samples were analyzed with regard to nitrate/nitrite concentration enzymatically as described in Amtliche Sammlung von Untersuchungsverfahren §64 Lebensmittel-und Futtermittelgesetzbuch (LFGB; German Food and Feed Act) (L 07.00-60) and the results are depicted in FIG. 23.
1) *S. vitulinus* CHCC10896—spike
2) *S. vitulinus* CHCC10896—feed
3) *S. carnosus*

CONCLUSION

It could be clearly shown, that the 2-phase fermentation with continuous nitrate feeding during the second low aerated phase of the process is leading to a significant improvement of nitrate reductase activity, respectively, of the ability to convert

| Strain | Batch | Active/g | CV | Total/g | CV | Active/Total | SD |
|---|---|---|---|---|---|---|---|
| *S. vitulinus* CHCC10896 | Spike fermentation | 1.03E+12 | 3.2% | 1.13E+12 | 3.0% | 91% | 0.2% |
| *S. vitulinus* CHCC10896 | 2-phase fermentation | 3.47E+11 | 1.8% | 4.52E+11 | 1.2% | 77% | 0.4% |

CV: Coefficient of variatio.
SD: Standard deviation.

brownish metmyoglobin into its red derivative nitrosylmyoglobin compared to the standard fermentation of *Staphylococcus carnosus* strain A. When only one high concentrated nitrate spike were given at the beginning of the second phase (spike fermentation) the intensity of the red color, as determined by the a*-value according to the L*a*b*-system of the resulting sausage is higher than that of the sausage prepared with *Staphylococcus carnosus* produced by standard fermentation but significantly lower than the red color intensity of the sausage prepared with the strain subjected to the two-phase fermentation method according to the present invention (with continuous nitrate feeding during the second phase of the two-phase fermentation method). The photographic documentation reflects these determinations showing a sausage prepared with the feed fermentation produced *Staphylococcus vitulinus*. In comparison the 2-phase fermentation with a nitrate spike at the beginning of the anaerobic growth phase, does not lead to any improvement of nitrate reductase activity as the red color intensity is comparable to the red color intensity of the sausage prepared with the *Staphylococcus carnosus* strain A fermented by standard fermentation. This is also reflected by the nitrate and nitrite concentration within the meat samples after incubation prior to cooking. The strain fermented according to the 2-phase fermentation procedure is able to reduce nitrate into nitrite at the given temperature and time period of fermentation whereas CHCC10896 fermented by spike fermentation does not reduce nitrate significantly into nitrite. Without wishing to be bound by theory, it is contemplated that a continuous nitrate feeding is needed to maintain a high level of expression of the nar operon responsible for nitrate reduction.

Deposits and Expert Solution

The applicant requests that a sample of the deposited micro-organisms stated below may only be made available to an expert, until the date on which the patent is granted.

The *Staphylococcus vitulinus* strain *CHCC*10896 was deposited on 2012-03-15 at DSMZ-Deutsche Sammlung von Mikroorganismen und Zellkulturen GmbH, Inhoffenstr. 7B, D-38124 Braunschweig and given the accession No.: DSM 25789.

The *Staphylococcus vitulinus* strain *CHCC*11576 was deposited on 2013-06-11 at DSMZ-Deutsche Sammlung von Mikroorganismen und Zellkulturen GmbH, Inhoffenstr. 7B, D-38124 Braunschweig and given the accession No.: DSM 27311.

The deposits were made according to the Budapest treaty on the international recognition of the deposit of microorganisms for the purposes of patent procedure.

REFERENCES

WO2010/067148

The invention claimed is:

1. A method for increasing the nitrate reductase activity of a *Staphylococcus* strain having nitrate reductase activity comprising the steps of
   a) fermenting the strain in the absence of nitrate under aerobic conditions;
   b) fermenting the strain under anaerobic or oxygen limiting conditions while continuously feeding nitrate to the fermentation medium; and
   c) optionally pelletizing and optionally freeze-drying the strain.

2. The method according to claim 1, wherein the *Staphylococcus* strain having nitrate reductase activity is a *Staphylococcus vitulinus* strain or a *Staphylococcus carnosus* strain.

3. The method according to claim 2, wherein the *Staphylococcus vitulinus* strain is selected from the group consisting of the *Staphylococcus vitulinus* strain CHCC10896 that was deposited with the Deutsche Sammlung von Mikroorganismen und Zellkulturen (DSMZ) under the accession no. DSM 25789, the *Staphylococcus vitulinus* strain CHCC11576 that was deposited with the Deutsche Sammlung von Mikroorganismen und Zellkulturen (DSMZ) under the accession no. DSM 27311, and mutants derived thereof.

4. A method for reddening of a food product comprising the steps of
   a) pre-treating a *Staphylococcus* strain having nitrate reductase activity according to the method of claim 1;
   b) adding the pre-treated *Staphylococcus* strain to a meat product; and
   c) fermenting, ripening or curing the meat product with the pre-treated *Staphylococcus* strain.

5. The method according to claim 4, wherein the food product is a meat product.

6. The method according to claim 4, wherein the *Staphylococcus* strain is a *Staphylococcus vitulinus* strain or a *Staphylococcus carnosus* strain.

7. The method according to claim 6, wherein the *Staphylococcus vitulinus* strain is selected from the group consisting of the *Staphylococcus vitulinus* strain CHCC10896 that was deposited with the Deutsche Sammlung von Mikroorganismen und Zellkulturen (DSMZ) under the accession no. DSM 25789, the *Staphylococcus vitulinus* strain CHCC11576 that was deposited with the Deutsche Sammlung von Mikroorganismen und Zellkulturen (DSMZ) under the accession no. DSM 27311, and mutants derived thereof.

* * * * *